(12) United States Patent
Zhang et al.

(10) Patent No.: US 12,252,687 B2
(45) Date of Patent: *Mar. 18, 2025

(54) RECOMBINANT YEAST AND USE THEREOF

(71) Applicants: Tianjin Institute of Industrial Biotechnology, Chinese Academy of Sciences, Tianjin (CN); Institute of Chinese Materia Medica, China Academy of Chinese Medical Sciences, Beijing (CN)

(72) Inventors: Xueli Zhang, Tianjin (CN); Luqi Huang, Beijing (CN); Zhubo Dai, Tianjin (CN); Dong Wang, Tianjin (CN); Lili Zhang, Tianjin (CN); Juan Guo, Beijing (CN); Yi Liu, Tianjin (CN)

(73) Assignees: Tianjin Institute of Industrial Biotechnology, Chinese Academy of Sciences, Tianjin (CN); Institute of Chinese Materia Medica, China Academy of Chinese Medical Sciences, Beijing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/456,333

(22) Filed: Aug. 25, 2023

(65) Prior Publication Data

US 2024/0010969 A1 Jan. 11, 2024

Related U.S. Application Data

(63) Continuation of application No. 17/812,157, filed on Jul. 12, 2022, now abandoned, which is a continuation of application No. 16/347,552, filed as application No. PCT/CN2017/109029 on Nov. 2, 2017, now Pat. No. 11,421,199.

(30) Foreign Application Priority Data

Nov. 4, 2016 (CN) .......................... 201610961269.5

(51) Int. Cl.
*C12N 1/18* (2006.01)
*C12N 9/10* (2006.01)
*C12N 9/88* (2006.01)
*C12R 1/865* (2006.01)

(52) U.S. Cl.
CPC .............. *C12N 1/18* (2013.01); *C12N 1/185* (2021.05); *C12N 9/1085* (2013.01); *C12N 9/88* (2013.01); *C12Y 205/0101* (2013.01); *C12Y 402/03023* (2013.01); *C12N 2500/05* (2013.01); *C12N 2500/10* (2013.01); *C12N 2500/32* (2013.01); *C12N 2500/34* (2013.01); *C12N 2500/38* (2013.01); *C12R 2001/865* (2021.05)

(58) Field of Classification Search
CPC . C12N 9/88; C12N 9/1085; C12Y 402/03023
See application file for complete search history.

(56) References Cited

U.S. PATENT DOCUMENTS

2015/0079646 A1   3/2015   Nielsen et al.

FOREIGN PATENT DOCUMENTS

| CN | 101928716 A | 12/2010 |
|---|---|---|
| CN | 103820344 A | 5/2014 |
| JP | 6-261741 A | 9/1994 |
| JP | 2008-507974 A | 3/2008 |
| WO | WO 2013/102554 A1 | 7/2013 |
| WO | WO/2016/029153 A1 | 2/2016 |

OTHER PUBLICATIONS

Albertsen, Line et al., "Diversion of Flux toward Sesquiterpene Production in *Saccharomyces cerevisiae* by Fusion of Host and Heterologous Enzymes" Applied and Environmental Microbiology, Feb. 2011, pp. 1033-1040, vol. 77, No. 3.
Aranda, Agustin et al., "Response to acetaldehyde stress in the yeast *Saccharomyces cerevisiae* involves a strain-dependent regulation of several ALD genes and is mediated by the general stress response pathway" Yeast, 2003, pp. 747-759, vol. 20.
Baadhe et al. "Combination of ERG9 Repression and Enzyme Fusion Technology for Improved Production of Amorphadjene in *Saccharomyces cerevisiae*". Journal of Analytical Methods in Chemistry, vol. 2013, Aug. 12, 2013.
Bennett, Mark H. et al., "Cloning and expression of sesquiterpene synthase genes from lettuce (*Lactuca sativa* L.)" Phytochemistry, 2002, pp. 255-261, vol. 60.
Brodelius, Maria et al., "Fusion of farnesyldiphosphate synthase and epi-aristolochene synthase, a sesquiterpene cyclase involved in capsidiol biosynthesis in *Nicotiana tabacum*" Eur. J. Biochem, 2002, pp. 3570-3577, vol. 269.
Chen, Yun et al., "Establishing a platform cell factory through engineering of yeast acetyl-CoA metabolism" Metabolic Engineering, 2013, pp. 48-54, vol. 15.
Entian et al., 25 Yeast Genetic Strain and Plasmid Collections, Methods in Microbiology 36 (2007), pp. 629-666.
Faraldos, Juan A. et al., "Conformational analysis of (+)-germacrene A by variable-temperature NMR and NOE spectroscopy" Tetrahedron, 2007, pp. 7733-7742, vol. 63.
Göpfert, Jens C. et al., "Identification, functional characterization and developmental regulation of sesquiterpene synthases from sunflower capitate glandular trichomes" BMC Plant Biology, 2009, pp. 1-18, vol. 9, No. 86.

(Continued)

*Primary Examiner* — Suzanne M Noakes
(74) *Attorney, Agent, or Firm* — Knobbe Martens Olson & Bear LLP

(57) ABSTRACT

Provided is a recombinant yeast expressing germacrene A synthetase or a fusion protein thereof, wherein the fusion protein is germacrene A synthetase and farnesyl pyrophosphate synthase. The recombinant yeast improves the yield of germacrene A, and is suitable for the industrialized production of β-elemene and/or germacrene A.

25 Claims, 1 Drawing Sheet
Specification includes a Sequence Listing.

(56) References Cited

OTHER PUBLICATIONS

Göpfert et al., "Identification and Functional Characterization of a new Sunflower Germacrene A Synthase (HaGAS3)", Natural Product Communications, 2010, 5(5):709-715.

Hong et al., Identification of gene targets eliciting improved alcohol tolerance in *Saccharomyces cerevisiae* through inverse metabolic engineering, Journal of Biotechnology 149 (2010), pp. 52-59.

Hu et al., "Approaching a complete repository of sequence-verified protein-encoding clones for *Saccharomyces cerevisiae*", Genome Res., 2007, 17(4):536-543.

Hu, Yating et al., "Metabolic engineering of *Saccharomyces cerevisiae* for production of germacrene A, a precursor of beta-elemene" J Ind Microbiol Biotechnol, 2017, pp. 1065-1072, vol. 44.

Liu et al., "Reconstitution of the Costunolide Biosynthetic Pathway in Yeast and Nicotiana benthamiana" PlosON E, Aug. 2011, PLoS One 6(8): e23255. 12 pages.

Luo et al. "Engineered Biosynthesis of Natural Products in Heterologous Hosts". Chemical Society Reviews Journal, Aug. 7, 2015.

Majdi, Mohammad et al., "Biosynthesis and localization of parthenolide in glandular trichomes of feverfew (*Tanacetum parthenium* L. *Schulz bip.*)" Phytochemistry, 2011, pp. 1739-1750, vol. 72.

Nguyen et al. "Biochemical Conservation and Evolution of Germacrene A Oxidase in Asteraceae". The Journal of Biological Chemistry, vol. 258, No. 22, May 28, 2010.

Özaydin et al. "Caroteniod-based phenotypic screen of the yeast deletion collection reveals new genes with roles in isoprenoid production". Metabolic Engineering Journal, pp. 174-183, Aug. 17, 2012.

Trenchard et al., De novo production of the key branch point benzylisoquinoline alkaloid reticuline in yeast, Metab4-olic Engineering 31 (2015), pp. 74-83.

Zhang, Yan et al., "Progress of heterologous expression of terpenes in *Saccharomyces cerevisiae*" Chemical Industry and Engineering Progress, Dec. 2014, pp. 1265-1270, vol. 33, No. 5.

Zhou et al. Modular Pathway Engineering of Diterpenoid Synthases and the Mevalonic Acid Pathway for Miltiradiene Production. Journal of the American Chemistry Society, Jan. 26, 2012.

"Tanacetum parthenium germacrene A synthase (GAS) mRNA, complete eds" Gene Bank: J F819848.1—Retrieved from < https://www.ncbi.nlm.nih.gov/nuccore/JF819848.1 > on Feb. 27, 2023.

Office Action for Japanese Patent Application No. 2019-544968 dated Jul. 28, 2020.

Supplementary European Search Report for EP 17867973 dated May 20, 2020.

International Search Report for PCT/CN2017/109029 dated Feb. 11, 2018.

RECOMBINANT YEAST AND USE THEREOF

CROSS REFERENCE TO RELATED APPLICATIONS

This application is a continuation of U.S. patent application Ser. No. 17/812,157, filed Jul. 12, 2022, which is a continuation of U.S. patent application Ser. No. 16/347,552, filed May 3, 2019, now U.S. Pat. No. 11,421,199, which is the U.S. National Phase Application of PCT International Application Number PCT/CN2017/109029, filed on Nov. 2, 2017, designating the United States of America and published in the Chinese language, which is an International Application of and claims the benefit of priority to Chinese Patent Application No. 201610961269.5, filed on Nov. 4, 2016. The disclosures of the above-referenced applications are hereby expressly incorporated by reference in their entireties.

INCORPORATION OF THE SEQUENCE LISTING

The material in the accompanying sequence listing is hereby incorporated by reference into this application. The accompanying sequence listing XML file, named SeqList-BSIP004.001C2.xml, was created on Aug. 24, 2023 and is 120,999 bytes.

FIELD OF THE INVENTION

The present invention relates to the field of biochemical industry, in particular to a recombinant strain, and synthesizing β-elemene according to a recombinant microbial method.

BACKGROUND OF THE INVENTION

β-elemene (beta-elemene) is a volatile sesquiterpene compound with tulip flavor, which is an active pharmaceutical ingredient (API) for first class new cancer drugs of China. At present, it is mainly separated and extracted from plants such as *Curcuma aromatica* and *Curcuma zedoary*, but this method has many disadvantages, including low content of β-elemene and large difference among plants, difficulty in product purification, long plant growth cycle, and serious damage to biological resources, especially wild resources.

By utilizing the principles of synthetic biology, designing and modifying microbial strains to produce natural products has been internationally recognized as one of the most promising methods, for example, the yield of taxadiene, the precursor of paclitaxel, in *E. coli* has reached 1000 mg/L (Parayil KuMaran AjikuMar et al., 2010, Science, 330: 70-74); levopimaradiene, the precursor of ginkgolides, has reached a yield of 700 mg/L in the engineered *E. coli* (Effendi Leonard et al., 2010, PNAS, 107(31): 13654-13659); the yield of artemisinic acid, the precursor of artemisinin in engineered yeast is up to 25 g/L (Paddon C J et al., 2013, Nature, 496 (7446): 528-531); and currently there are related studies on the biosynthesis of drug molecules such as artemisinin, paclitaxel and tanshinone in China.

In nature, farnesyl pyrophosphate (FPP) can be catalyzed by germacrene A synthetase (GMAS) to synthesize germacrene A. Germacrene A is thermally unstable and prone to intramolecular thermal rearrangement to give β-elemene. At present, some studies have been carried out on the production of germacrene A, the precursor of β-elemene, by using recombinant strains, but the yields are low and cannot meet the requirements of industrial applications. For example, Gao Yunyun et al. constructed a biosynthetic pathway of germacrene A in *E. coli*, and the highest yield of germacrene A synthesized by the resulted recombinant strain was only 6.32 mg/L, which is still far from industrialization (Studies on the microbial biosynthesis of the precursor of β-elemene—germacrene A, Gao Yunyun, 2012, Hangzhou Normal University).

SUMMARY OF THE INVENTION

An object of the present invention is to provide a recombinant strain.

The recombinant strain provided herein is a yeast comprising or expressing germacrene A synthetase or a fusion protein of germacrene A synthetase/n vivo.

The fusion protein of germacrene A synthetase comprises the germacrene A synthetase and farnesyl pyrophosphate synthase.

The above recombinant strains are classified into one or more kinds depending on the host source of gene for the fusion protein, and a nucleic acid encoding the fusion protein comprises a nucleic acid encoding the germacrene A synthetase and a nucleic acid encoding the farnesyl pyrophosphate synthase.

The fusion protein has one or more encoding nucleic acids.

Among the plurality of nucleic acids encoding the fusion protein, at least two nucleic acids encoding the germacrene A synthetase are derived from different hosts, and at least two nucleic acids encoding the farnesyl pyrophosphate synthase are derived from different hosts.

The difference of hosts from which the gene is derived in the present invention means that the hosts from which the gene is originally derived are different. The gene for germacrene A synthetase of the present invention can be obtained by cloning from a plant or microorganism known to contain germacrene A synthetase, for example, it can be selected from *Helianthus annuus* L., *Tanacetum parthenium*, lettuce (*Lactuca sativa* Linn.), *Artemisia carvifolia*, cyanobacteria, etc. The gene for farnesyl pyrophosphate synthase (farnesyl diphosphate synthase) can be obtained by cloning from a plant or microorganisms known to contain farnesyl pyrophosphate synthase, for example, it can be selected from *Salvia miltiorrhiza*, Yeast, *Acanthopanax senticosus* (Rupr. Maxim.) Harms), *Eucommiaulmoides* Oliv., etc.

The nucleic acid encoding the germacrene A synthetase comprises a nucleic acid represented by SEQ ID NO: 3 or a nucleic acid represented by positions 13-1686 of SEQ ID NO: 12.

The nucleic acid encoding the farnesyl pyrophosphate synthase comprises a nucleic acid represented by SEQ ID NO: 2 or a nucleic acid represented by positions 1-1056 of SEQ ID NO: 11.

In the recombinant strain, the fusion protein further comprises a linker peptide for linking the germacrene A synthetase with the farnesyl pyrophosphate synthase.

The linker peptide is selected from GGGS (SEQ ID NO: 15), YGQ (3A001), PGGH (4A001) (SEQ ID NO: 16), YRSQI (5A002) (SEQ ID NO: 17), VIPFIS (6A005) (SEQ ID NO: 18), FLYLKF (6B004) (SEQ ID NO: 19), WRFSPKLQ (8A005) (SEQ ID NO: 20) or HHVQESQ-CISTV (12A003) (SEQ ID NO: 21).

In the above recombinant strain, comprising or expressing germacrene A synthetase or a fusion protein of germacrene A synthetase/n vivo is introducing a nucleic acid encoding the germacrene A synthetase or a nucleic acid encoding the fusion protein into yeast;

And/or, introducing the nucleic acid encoding the germacrene A synthetase into the yeast is introducing an expression cassette comprising the nucleic acid encoding the germacrene A synthetase into the yeast;

Introducing the nucleic acid encoding the fusion protein into the yeast is introducing an expression cassette comprising the nucleic acid encoding the fusion protein into the yeast;

And/or, the expression cassette comprises the nucleic acid encoding the germacrene A synthetase contains a promoter, a nucleic acid encoding the germacrene A synthetase, and a terminator;

And/or, the expression cassette comprises the nucleic acid encoding the fusion protein contains a promoter, a nucleic acid encoding the fusion protein, and a terminator;

Or, the promoter is selected from TEF1 or MF1 or PGK1; the terminator is CYC1 or ADH1;

Or, the promoter is TEF1, and the terminator is CYC1;
Or, the promoter is MF1, and the terminator is CYC1;
Or, the promoter is PGK1 and the terminator is ADH1.

Hereinbefore, the promoter TEF1 comprises the sequence represented by SEQ ID NO: 4; the promoter MF1 comprises the sequence represented by SEQ ID NO: 1; and the terminator CYC1 comprises the sequence represented by SEQ ID NO: 5.

In the above recombinant strain, the recombinant strain further expresses one or more marker genes; and/or the marker gene is selected from his3 or trp1.

In the above recombinant strain, the expression cassette comprising the nucleic acid encoding the germacrene A synthetase is introduced into the yeast via a vector expressing the expression cassette of the nucleic acid encoding the germacrene A synthetase.

The expression cassette comprising the nucleic acid encoding the fusion protein is introduced into the yeast via a vector expressing the expression cassette comprising the nucleic acid encoding the fusion protein.

In the above recombinant strain, the expression cassette of the nucleic acid encoding the germacrene A synthetase is introduced into the yeast in the form of plasmid;

Or, the expression cassette of the nucleic acid encoding the fusion protein is introduced into the yeast in the form of plasmid and/or being integrated into a chromosome.

In the examples of the invention,
the fusion protein is selected from at least one of the following: SynSmFPS-GGGS (SEQ ID NO: 15)-STpGMAS, SynSmFPS-YGQ-STpGMAS, SynSmFPS-PGGH (SEQ ID NO: 16)-STpGMAS, SynSmFPS-YRSQI (SEQ ID NO: 17)-STpGMAS, SynSmFPS-VIPFIS (SEQ ID NO: 18)-STpGMAS, SynSmFPS-FLYLKF (SEQ ID NO: 19)-STpGMAS, SynSmFPS-WRFSPKLQ (SEQ ID NO: 20)-STpGMAS, SynSmFPS-HHVQESQCISTV (SEQ ID NO: 21)-STpGMAS, SynSmFPS-WRFSPKLQ (SEQ ID NO: 20)-STpGMAS, ERG20-GGGS (SEQ ID NO: 15)-LsLTC2;

The fusion protein is preferably SynSmFPS-8A005-STpGMAS;

Particularly preferred fusion proteins are three kinds of fusion proteins: SynSmFPS-WRFSPKLQ (8A005) (SEQ ID NO: 20)-STpGMAS, ERG20-GGGS (SEQ ID NO: 15)-LsLTC2, SynSmFPS-GGGS (SEQ ID NO: 15)-STpGMAS;

The expression cassette expressing the nucleic acid encoding the fusion protein is selected from at least one of the following:

$P_{TEF1}$-SynSmFPS-GGGS-STpGMAS-$T_{CYC1}$, (SEQ ID NO: 15)

$P_{TEF1}$-SynSmFPS-YGQ-STpGMAS-$T_{CYC1}$, $P_{TEF1}$-SynSmFPS-PGGH-STpGMAS-$T_{CYC1}$, (SEQ ID NO: 16)

$P_{TEF1}$-SynSmFPS-YRSQI-STpGMAS-$T_{CYC1}$, (SEQ ID NO: 17)

$P_{TEF1}$-SynSmFPS-VIPFIS-STpGMAS-$T_{CYC1}$, (SEQ ID NO: 18)

$P_{TEF1}$-SynSmFPS-FLYLKF-STpGMAS-$T_{CYC1}$, (SEQ ID NO: 19)

$P_{TEF1}$-SynSmFPS-WRFSPKLQ (8A005)-STpGMAS-$T_{CYC1}$, (SEQ ID NO: 20)

$P_{TEF1}$-SynSmFPS-HHVQESQCISTV-STpGMAS-$T_{CYC1}$, (SEQ ID NO: 21)
or $P_{MF1}$-SynSmFPS-WRFSPKLQ (8A005)-STpGMAS-$T_{CYC1}$, (SEQ ID NO: 20)

The expression cassette expressing the nucleic acid encoding the fusion protein is preferably $P_{MF1}$-SynSmFPS-8A005-STpGMAS-$T_{CYC1}$;

Particularly preferred expression cassettes expressing the nucleic acid encoding the fusion protein are the following three kinds: $P_{MF1}$-SynSmFPS-8A005-STpGMAS-$T_{CYC1}$, $P_{PGK}$1-ERG20-GGGS (SEQ ID NO: 15)-LsLTC2-$T_{ADH1}$ and $P_{TEF1}$-SynSmFPS-GGGS (SEQ ID NO: 15)-STpGMAS-$T_{CYC1}$.

The vector expressing the expression cassette of the nucleic acid encoding the germacrene A synthetase is selected from the following:

pRS313-LEU2-$P_{TEF1}$-STpGMAS-$T_{CYC1}$,
pRS425-LEU2-$P_{TEF1}$-STpGMAS-$T_{CYC1}$.

The vector expressing the expression cassette of the nucleic acid encoding the germacrene A synthetase is selected from the following:

pRS425-LEU2-$P_{TEF1}$-SynSmFPS-GGGS-STpGMAS-$T_{CYC1}$, (SEQ ID NO: 15)

pRS425-LEU2-$P_{TEF1}$-SynSmFPS-YGQ-STpGMAS-$T_{CYC1}$, pRS425-LEU2-$P_{TEF1}$-SynSmFPS-PGGH-STpGMAS-$T_{CYC1}$, (SEQ ID NO: 16)

pRS425-LEU2-$P_{TEF1}$-SynSmFPS-YRSQI-STpGMAS-$T_{CYC1}$, (SEQ ID NO: 17)

pRS425-LEU2-$P_{TEF1}$-SynSmFPS-VIPFIS-STpGMAS-$T_{CYC1}$, (SEQ ID NO: 18)

pRS425-LEU2-$P_{TEF1}$-SynSmFPS-FLYLKF-STpGMAS-$T_{CYC1}$, (SEQ ID NO: 19)

pRS425-LEU2-$P_{TEF1}$-SynSmFPS-WRFSPKLQ-STpGMAS-$T_{CYC1}$, (SEQ ID NO: 20)
or pRS425-LEU2-$P_{TEF1}$-SynSmFPS-HHVQESQCISTV-STpGMAS-$T_{CYC1}$, (SEQ ID NO: 21)
or pRS425-LEU2-$P_{MF1}$-SynSmFPS-WRFSPKLQ-STpGMAS-$T_{CYC1}$. (SEQ ID NO: 20)

The above gene expression cassette of the fusion protein integrated into the chromosome is selected from $P_{TEF1}$-

SynSmFPS-GGGS (SEQ ID NO: 15)-STpGMAS-$T_{CYC1}$ and $P_{PGK1}$-ERG20-GGGS (SEQ ID NO: 15)-LsLTC2-$T_{ADH1}$.

In the above recombinant strain, the yeast is a strain obtained by increasing content and/or activity of alcohol dehydrogenase, acetaldehyde dehydrogenase and acetyl-CoA synthetase in an original yeast.

The strain obtained by increasing the content and/or activity of alcohol dehydrogenase, acetaldehyde dehydrogenase and acetyl-CoA synthetase in the original yeast relates to increasing copy numbers of a nucleic acid encoding the alcohol dehydrogenase, a nucleic acid encoding the acetaldehyde dehydrogenase and a nucleic acid encoding the acetyl-CoA synthetase in the original yeast.

In the above recombinant strain, increasing copy numbers of the nucleic acid encoding the alcohol dehydrogenase, the nucleic acid encoding the acetaldehyde dehydrogenase and the nucleic acid encoding the acetyl-CoA synthetase in the original yeast is introducing an expression cassette of the nucleic acid encoding the alcohol dehydrogenase, an expression cassette of the nucleic acid encoding the acetaldehyde dehydrogenase, an expression cassette of the nucleic acid encoding the acetyl-CoA synthetase, and another said marker gene (his3) into the original yeast by homologous recombination.

In the above recombinant strain, the original yeast is Saccharomyces cerevisiae; and/or said Saccharomyces cerevisiae is Saccharomyces cerevisiae NK2-SQ.

One of the marker genes is TRP1; another of the marker genes is HIS3.

Gene ADH2 of the above alcohol dehydrogenase comprises the sequence represented by SEQ ID NO: 6, gene ALD6 of the acetaldehyde dehydrogenase comprises the sequence represented by SEQ ID NO: 7, and gene ACS1 of the acetyl-CoA synthetase comprises the sequence represented by SEQ ID NO: 8.

Constructions of the recombinant strain and each of the required vectors and fragments of the present invention are shown in the examples.

In the examples of the invention, the recombinant strains are specifically as follows: Recombinant strain ELE-001 is a strain obtained by introducing pRS313-LEU2-$P_{TEF1}$-STpGMAS-$T_{CYC1}$ into yeast FPP-001;

Recombinant strain ELE-002 is a strain obtained by introducing pRS425-LEU2-$P_{TEF1}$-STpGMAS-$T_{CYC1}$ into yeast FPP-001;

Recombinant strain ELE-011, which is a strain obtained by introducing pRS425-LEU2-$P_{TEF1}$-SynSmFPS-GGGS (SEQ ID NO: 15)-STpGMAS-$T_{CYC1}$ into yeast FPP-001;

Recombinant strain ELE-012 is a strain obtained by introducing pRS425-LEU2-$P_{TEF1}$-SynSmFPS-3A001-STpGMAS-$T_{CYC1}$ into yeast FPP-001;

Recombinant strain ELE-013 is a strain obtained by introducing pRS425-LEU2-$P_{TEF1}$-SynSmFPS-4A001-STpGMAS-$T_{CYC1}$ into yeast FPP-001;

Recombinant strain ELE-014 is a strain obtained by introducing pRS425-LEU2-$P_{TEF1}$-SynSmFPS-5A002-STpGMAS-$T_{CYC1}$ into yeast FPP-001;

Recombinant strain ELE-015 is a strain obtained by introducing pRS425-LEU2-$P_{TEF1}$-SynSmFPS-6A005-STpGMAS-$T_{CYC1}$ into yeast FPP-001;

Recombinant strain ELE-016 is a strain obtained by introducing pRS425-LEU2-$P_{TEF1}$-SynSmFPS-6B004-STpGMAS-$T_{CYC1}$ into yeast FPP-001;

Recombinant strain ELE-017 is a strain obtained by introducing pRS425-LEU2-$P_{TEF1}$-SynSmFPS-8A005-STpGMAS-$T_{CYC1}$ into yeast FPP-001;

Recombinant strain ELE-018 is a strain obtained by introducing pRS425-LEU2-$P_{TEF1}$-SynSmFPS-12A003-STpGMAS-$T_{CYC1}$ into yeast FPP-001;

Recombinant strain ELE-019 is a strain obtained by introducing pRS425-LEU2-$P_{MF}$1-SynSmFPS-8A005-STpGMAS-$T_{CYC1}$ into yeast FPP-001;

Recombinant strain ELE-020 is a strain obtained by introducing pRS425-LEU2-$P_{MF1}$-SynSmFPS-8A005-STpGMAS-$T_{CYC1}$, and then introducing $P_{PGK1}$-ERG20-GGGS(SEQ ID NO: 15)-LsLTC2-$T_{ADH1}$, $P_{TEF1}$-SynSmFPS-GGGS (SEQ ID NO: 15)-STpGMAS-$T_{CYC1}$, rDNA-TRP1-up and rDNA-TRP1-down by homologous recombination into yeast FPP-001.

The above yeast FPP-001 is a strain obtained by introducing NDT80-HIS3-up, $P_{PGK1}$-ADH2-$T_{ADH1}$, $P_{TDH3}$-ACS1-$T_{TPI1}$, $P_{TEF1}$-ALD6-$T_{CYC1}$ and NDT80-HIS3-down into Saccharomyces cerevisiae.

Wherein, recombinant strain ELE-020 is Saccharomyces cerevisiae CGMCC No. 14829, which also falls within the protection scope of the present invention.

This recombinant strain ELE-020 is deposited on Oct. 20, 2017 at the China General Microbiological Culture Collection Center, CGMCC. The deposition address is Building 3, No. 1 West Beichen Road, Chaoyang District, Beijing. The strain name is: Saccharomyces cerevisiae; the latin name thereof is: Saccharomyces cerevisiae; and the deposition number thereof is: CGMCC No. 14829.

The use of the above recombinant strain for the production of β-elemene and/or germacrene A also falls within the protection scope of the present invention.

A third object of the present invention is to provide a method for producing germacrene A.

The method provided by the invention includes the following steps: fermenting the above recombinant strain to obtain germacrene A.

A fourth object of the present invention is to provide a method for producing β-elemene.

The method provided by the invention includes the following steps:

1) Fermenting the recombinant strain to obtain a fermentation product;
2) Extracting the fermentation product with an organic solution, and collecting the organic phase;
3) Heating the organic phase to obtain β-elemene.

In the above methods, the fermentation relates to: firstly culturing the recombinant strain in a seed medium to obtain a seed liquid; then inoculating the seed liquid into a fermentation medium for fermentation culture, and recording a product of the fermentation culture as a fermentation system.

In the above methods, during the fermentation culture, a fed-batch medium is added into the fermentation system; preferably, when the dissolved oxygen value in the fermentation system is greater than 60%, a fed-batch medium is added into the fermentation system until glucose concentration of the fermentation system reaches 5 g/L.

In the above methods, a formulation of the seed medium and the fermentation medium contains per L volume: 25 g of glucose, 15 g of ammonium sulfate, 6.15 g of magnesium sulfate heptahydrate, 0.72 g of zinc sulfate heptahydrate, 8 g of potassium dihydrogen phosphate, 2 mL of calcium chloride mother liquid, 10 mL of trace metal salt mother liquid; 12 mL of vitamin mother liquid, 1 g of tryptophan; and the balance of water.

The calcium chloride mother liquid is 19.2 g/L aqueous solution of calcium chloride dihydrate.

A formulation of the trace metal salt mother liquid contains per L volume: 19.1 g of disodium ethylenediamine tetraacetate; 10.2 g of zinc sulfate heptahydrate; 0.5 g of manganese chloride tetrahydrate; 0.86 g of cobalt chloride hexahydrate; 0.78 g of copper sulfate pentahydrate; 0.56 g of sodium molybdate dihydrate; 5.12 g of iron sulphite heptahydrate; and the balance of water.

The formulation of the vitamin mother liquid contains per L volume: 0.05 g of biotin; 0.2 g of sodium p-aminobenzoate; 1 g of niacin; 1 g of calcium pantothenate; 1 g pyridoxine hydrochloride; 1 g of thiamine hydrochloride; 25 g of inositol; and the balance of water.

The formulation of the fed-batch medium contains per L volume: 800 g of glucose, 5.125 g of magnesium sulfate heptahydrate, 3.5 g of potassium sulfate, 0.28 g of sodium sulfate, 9 g of potassium dihydrogen phosphate and 1 g of tryptophan; and the balance of water.

Before the fermentation, the following steps are further included:
a) Activating the recombinant strain in a solid selective medium;
b) After a shaking culture in a liquid selective medium, transferring the recombinant strain into a seed medium for culturing to give a seed liquid.

Wherein, the solid or liquid selective medium is a SD-Ura-His-Leu medium.

The culture conditions in the above step b) are 30° C., 250 rpm; the inoculation step involves a flame loop inoculation.

Specifically, in the above fermentation method, the method for culturing the seed liquid is that: after the recombinant strain is activated, a monoclonal colony on the plate is picked up and inoculated into a test tube containing SD-Ura-His-Leu medium, and shaken at 250 rpm and cultured at 30° C. overnight; 500 μL of strain culture is pipetted into a 250 mL trigonal flask containing 50 mL of SD-Ura-His-Leu medium, and shaken at 250 rpm and cultured at 30° C. for 24 h; 2 mL of strain culture is respectively pipetted into three 1 L trigonal flasks containing 100 mL of seed medium, shaken at 250 rpm and cultured at 30° C. for 48 h.

In the above method for producing β-elemene, the organic solvent is n-dodecane; the heating condition is: heating at 100-380° C. for 1 hour.

DETAILED DESCRIPTION OF THE INVENTION

Unless otherwise specified, the experimental methods used in the following examples are conventional methods.

Unless otherwise specified, the materials, reagents and the like used in the following examples are commercially available.

Figure 1:
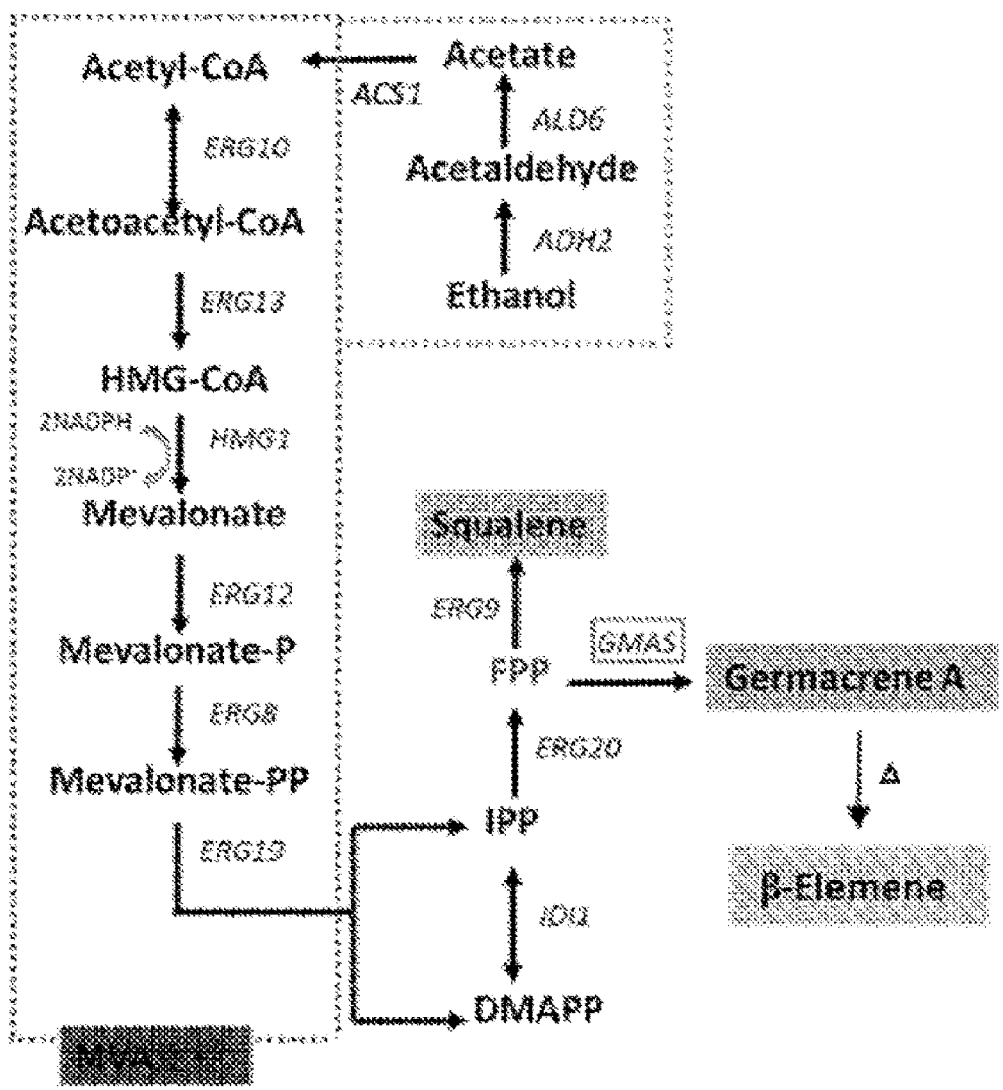
FIG. 1 shows the germacrene A biosynthetic pathway.

FIG. 1 shows the germacrene A biosynthetic pathway.

Example 1: Preparation of Target Genes and Plasmids Used

1. Preparation of Target Genes
(1) Acquisition of ADH2, ALD6, ASC1, MF1, TEF1 and CYC1

Genomic DNA of yeast NK2-SQ (China Journal of Chinese Materia Medica, Lin Tingting, Wang Dong, Dai Zhubo, Zhang Xueli, Huang Luqi, 2016, 41(6): 1008-1015) was extracted as a template, and was amplified by using the primers required in the gene amplification in Table 1 to obtain ADH2, ALD6, ASC1 gene fragments with the expected size, promoter MF1, TEF1 and terminator CYC1.

PCR amplification kit TAKARA PrimeSTAR®HS DNApolymerase was used to formulate an amplification system (TAKARA). The amplification system included: 5×PS Buffer 10 μL, dNTPMix 4 μL, primers 1 μL for each, genomic DNA template 1 μL, PrimeSTAR®HS polymerase (2.5 U/μL) 0.5 μL, distilled water supplemented to a total volume of 50 μL. The amplification conditions were: pre-denaturation at 98° C. for 3 minutes (1 cycle); denaturation at 9801 for 10 sec, annealing at 55° C. for 15 sec, extension at 72° C. for 2.5 min (30 cycles); and extension at 72° C. for 10 min (1 cycle).

TABLE 1

Primer sequences

| Gene fragment | Primer name | Primer sequence (5'→3') |
|---|---|---|
| ADH2 | SexA1-ADH2 | GCGACCWGGTATGTCTATTCCAGAAACTCAAAAAGC (SEQ ID NO: 22) |
| | ADH2-Asc1 | GCGGCGCGCCTTATTTAGAAGTGTCAACAACGTATC (SEQ ID NO: 23) |
| ALD6 | SexA1-ALD6 | TCGCGACCWGGTAAAACAATGACTAAGCTACACTTTGAC (SEQ ID NO: 24) |
| | ALD6-Asc1 | TCGCGGCGCGCCTTACAACTTAATTCTGACAGCT (SEQ ID NO: 25) |
| ACS1 | SexA1-ACS1 | TCGCGACCWGGTAAAACAATGTCGCCCTCTGCCGTACAATC (SEQ ID NO: 26) |
| | ACS1-Asc1 | TCGCGGCGCGCCTTACAACTTGACCGAATCAATTAG (SEQ ID NO: 27) |
| TEF1 | Sac11-TEF1 | GCGCCGCGGAGTGATCCCCCACACACCATAGCTT-SEQ ID NO: 28) |
| | TEF1-SexA1 | TGGCGACCWGGTTTTGTAATTAAAACTTAGATTAGA (SEQ ID NO: 29) |
| MF1 | BamH1-pMF1 | GCGGGATCCGGGAAGACATGCTTAACAAGAAGAT (SEQ ID NO: 30) |
| | pMF1-SexA1 | GCGACCTGGTTCTTTTAATCGTTTATATTGTGTAT (SEQ ID NO: 31) |

TABLE 1-continued

Primer sequences

| Gene fragment | Primer name | Primer sequence (5'→3') |
|---|---|---|
| CYC1 | AscI-CYC1 | GCGGCGCGCCCCGCTGATCCTAGAGGGCCGCATCA (SEQ ID NO: 32) |
| | CYC1-SacII | GCGCCGCGGGCGCGTTGGCCGATTCATTAATGCA (SEQ ID NO: 33) |

(2) Acquisition of Farnesyl Pyrophosphate Synthase Gene SynSmFPS from *Salvia miltiorrhiza* and Germacrene a Synthetase Gene STpGMA from *Tanacetum parthenium*

Nanjing GenScript Biotechnology Co., Ltd. designed full-length primers according to the sequences of SynSmFPS (SEQ ID NO: 2, derived from *Salvia miltiorrhiza*) and STpGMAS (SEQ ID NO: 3, derived from *Tanacetum parthenium*) genes, and the template DNA was formed by using OVERLAP method. The double-stranded DNAs of SynSmFPS (SEQ ID NO: 2) and STpGMAS (SEQ ID NO: 3) were obtained by PCR amplification method, and then the PCR products were transformed and cloned into a cloning vector pUC57 (Nanjing GenScript Biotechnology Co., Ltd.), and cloning plasmids of pUC57-SynSmFPS and pUC57-STpGMAS containing SynSmFPS gene and STPGMAS gene were constructed, respectively.

(3) Acquisition of Farnesyl Pyrophosphate Synthase Gene ERG20-GGGS (SEQ ID NO: 15) from Yeast and Germacrene a Synthetase Gene GGGS (SEQ ID NO: 15)-LsLTC2 from Lettuce 200 mg of lettuce leaves was taken and ground with liquid nitrogen, and then total RNA thereof was extracted by CTAB method (Cetyltrimethylammonium Bromide method): 1 ml of 2*CTAB extract (2% CTAB, 100 mM of Tris-HCl PH 8.0, 20 mM of EDTA solution (ethylenediamine tetraacetic acid), and 1.4M NaCl solution) was added into a 1.5 ml centrifuge tube. After being pre-heated at 65° C., 20 μL of 2-mercaptoethanol was added, and a small amount of lettuce leaf powder (about 50 mg) was added thereto, and then they were mixed well and kept at 65° C. for 10 min, shaken 5 times, centrifuged at 12,000 rpm for 10 min under 4° C.; the resulted supernatant was removed, extracted with an equal volume of chloroform/isoamyl alcohol, centrifuged at 12,000 rpm for 10 min under 4° C.; the obtained supernatant was removed, extracted with an equal volume of chloroform/isoamyl alcohol, centrifuged at 12,000 rpm for 10 min under 4° C.; the resulted supernatant was removed, extracted with ⅙ volume of chloroform/isoamyl alcohol, centrifuged at 15,000 rpm for 30 min under 4° C.; the obtained supernatant was removed, to which ¼ volume of 10 mol/L LiCl was added, kept at 4° C. overnight, centrifuged at 15,000 rpm for 30 min under 4° C.; the supernatant was discarded, and the obtained precipitate was washed twice with 75% ethanol and washed once with absolute ethanol, and placed on the super-clean bench for 15 min (room temperature); it was dissolved in 20 μL of milliQ DEPC-treated water (the solvent was milliQ pure water and the solute was diethyl pyrocarbonate, and the volume ratio diethyl pyrocarbonate:water was 1:1000), to which ¹/₁₀ volume of 2 mol/L NaAC (pH 4.0) and 2 volumes of absolute ethanol were added, kept at −20° C. for 2 h, and centrifuged at 12,000 rpm for 10 min under 4° C.; the resulted supernatant was discarded, and the obtained precipitate was washed twice with 75% ethanol and washed once with absolute ethanol, placed on a super-clean bench for 15 min (room temperature), to which 15 μL of milliQ DEPC-treated water was added to fully dissolve the precipitate, and stored at −70° C.

First-strand reverse transcription-PCR: a RNase-free PCR tube was taken, and the system was formulated according to a first strand reverse transcription kit (TaKaRa Biotechnology (Dalian) Co., Ltd.): Radom 6 Mers 2 μL, dNTP 1 μL, total RNA 1 μL (200 ng), H₂O 6 μL, Total 10 μL; a transient centrifugation was performed; PCR was carried out at 65° C. for 5 min; quenching it on ice and then adding the same into the following system for reaction (coming with the first chain reverse transcription kit): 5*primer Buffer 4 μL, RNAs Inhibiter 0.5 μL, R-Transcription 1 μL, H₂O 4.5 μL; transient centrifugation was performed, and a reaction was performed in a PCR instrument: 30° C. for 10 min, 42° C. for 60 min, 70° C. for 15 min, and kept at 4° C.

NK2-SQ genomic DNA and lettuce cDNA were used as templates, respectively, and amplified by using the primers in Table 2 to obtain about 1068 bp of ERG20-GGGS (SEQ ID NO: 15) (the one of positions 13-1686 in SEQ ID NO: 11 was ERG20) and 1688 bp of GGGS (SEQ ID NO: 15)-LsLTC2 (the one of positions 1-1056 in SEQ.ID NO.12 was LsLTC2).

The system was formulated according to the PCR amplification kit Phusion High-Fidelity PCR Master Mix with HF Buffer (purchased from NEB (Beijing) Co., Ltd.). The amplification system included: 5×Phusion HF Buffer 10 μL, dNTP (10 mM each dNTP) 1 μL, DNA template 20 ng, primers (10 μM) 1.5 μL for each, Phusion High-Fidelity DNA Polymerase (2.5 U/μL) 0.5 μL, and distilled water supplemented to a total volume of 50 μL. Amplification conditions: pre-denaturation at 98° C. for 3 min (1 cycle); denaturation at 98° C. for 10 sec, annealing at 58° C. for 10 sec, extension at 72° C. for 1 min (30 cycles); and extension at 72° C. for 10 min (1 cycle).

TABLE 2

Primer sequences

| Gene fragment | Primer name | Primer sequence (5'→3') |
|---|---|---|
| ERG20-GGGS (SEQ ID NO: 15) | SEXA1-ERG20 | GCGACCWGGTAAAACAATGGCTTCAGAAAAAGAAATT AGGAG (SEQ ID NO: 34) |
| | ERG20-GGGS (SEQ ID NO: 15) | CTTTCCCATAGAACCACCACCCTATTTGCTTCTCTTGT AAACTTTG (SEQ ID NO: 35) |

TABLE 2-continued

Primer sequences

| Gene fragment | Primer name | Primer sequence (5'→3') |
|---|---|---|
| GGGS (SEQ ID NO: 15)-LSLTC2 | GGGS (SEQ NO: 15)-LSLTC2 | GGTGGTGGTTCTATGGCAGCAGTTGACACTAA (SEQ ID NO: 36) |
| | LSLTC2-ASC1 | GCGGGCGCGCCTTACATGGATACAGAACCAACAAAT (SEQ ID NO: 37) |

2. Construction of Recombinant Plasmids (1) Plasmid pM2-ADH2

ADH2 obtained through amplification in the above "1. Preparation of target genes" and plasmid pM2-tHMG1 (described in Chinese patent ZL201310399947.X) were double enzyme digested by using SexA1 (purchased from NEB (Beijing) Co., Ltd.) and Asc1 (purchased from NEB (Beijing) Co., Ltd.) to obtain 1052 bp of ADH2 enzyme-digested product and 4738 bp of enzyme-digested plasmid pM2-tHMG1 backbone; the ADH2 enzyme-digested product was then ligated with the enzyme-digested plasmid pM2-tHMG1 backbone to obtain the recombinant plasmid pM2-ADH2.

(2) Plasmid pM4-ACS1

ACS1 obtained through amplification in the above "1. Preparation of target genes" and plasmid pM4-AtCPR1 (described in Chinese patent ZL201310399947.X) were double enzyme digested by using SexA1 and Asc1 to obtain 2201 bp of ACS1 enzyme-digested product and 5061 bp of enzyme-digested plasmid pM4-AtCPR1 backbone; the ACS1 enzyme-digested product was then ligated with the enzyme-digested plasmid pM4-AtCPR1 backbone to obtain the recombinant plasmid pM4-ACS1.

(3) Plasmid pM3-ALD6

ALD6 obtained through amplification in the above "1. Preparation of target genes" and plasmid pM3-ERG9 (described in Chinese patent ZL201310399947.X) were double enzyme digested by using SexA1 and Asc1 to obtain 1511 bp of ALD6 enzyme-digested product and 4598 bp of enzyme-digested plasmid pM3-ERG9 backbone; the ALD6 enzyme-digested product was then ligated with the enzyme-digested plasmid pM3-ERG9 backbone to obtain the recombinant plasmid pM3-ALD6.

(4) Construction of Plasmids pRS313-LEU2-$P_{TEF1}$-STpG-MAS-$T_{CYC1}$ and pRS425-LEU2-$P_{TEF1}$-STpGMAS-$T_{CYC1}$ TEF1 obtained through amplification in the above "1. Preparation of target genes" was enzyme digested by using SexA1, and 440 bp of TEF1 enzyme-digested product was obtained;

CYC1 obtained through amplification in the above "1. Preparation of target genes" was enzyme digested by using Asc1, and 322 bp of CYC1 enzyme-digested product was obtained;

pUC57-STpGMAS was enzyme digested by using SexA1 and Asc1, and 1694 bp of STpGMAS was recovered.

50 ng of each of the enzyme-digested products TEF1, CYC1 and STpGMAS was added into a ligation system including: 2 μL of 10×T4 DNA Ligase Reaction Buffer (NEB), 1 μL of T4 DNA Ligase (NEB, 400,000 cohesive end units/ml), distilled water supplemented to 20 μL; they reacted at room temperature for 2 hours to obtain a ligation product.

1 μL of the ligation product was added into a PCR system (Phusion High-Fidelity PCR Master Mix with HF Buffer kit, NEB) including: 5×Phusion HF Buffer 10 μL, dNTP (10 mM each dNTP) 1 μL, DNA template 20 ng, and primers Sac11-TEF1 and CYC1-Sac11 (10 μM) in Table 3, 1.5 μL for each, Phusion High-Fidelity DNA Polymerase (2.5 U/μL) 0.5 μL, and distilled water supplemented to a total volume of 50 μL. The amplification conditions were: pre-denaturation at 98° C. for 3 min (1 cycle); denaturation at 98° C. for 10 sec, annealing at 58° C. for 10 sec, extension at 72° C. for 1.5 min (30 cycles); and extension at 72° C. for 10 min (1 cycle). 2456 bp of PCR amplification product was obtained.

The amplification product was purified, and then enzyme digested by using SacII. The target fragment SacII-TEF1-STpGMAS-CYC1-SacII was recovered from gel, and prepared to use.

Plasmids pRS313 (Sikorski, R. S. and Hieter, P. 1989, Genetics 122 (1): 19-27) and pRS425 (Sikorski, R. S. and Hieter, P. 1989, Genetics 122 (1): 19-27) were enzyme digested with SacII, respectively, and 4967 bp of pRS313 vector fragment and 6849 bp of pRS425 vector fragment were obtained; 4 μL of NEB buffer and 1 μL of CIP dephosphorylation enzyme (NEB) were then added, and distilled water was supplemented to 40 μL; it was treated at 37° C. for 1 h, and EDTA with the final concentration of 10 μmol was added; it was kept at 65° C. for 30 min to terminate the reaction, and pRS313-SacII vector fragment and pRS425-SacII vector fragment were recovered from gel.

50 ng of each of the vector fragments pRS313-SacII, pRS425-SacII and SacII-TEF1-STpGMAS-CYC1-SacII obtained in the above step "1. Preparation of target genes" were respectively added into a ligation system including: 2 μL 10×T4 DNA Ligase Reaction Buffer (NEB)), 1 μL T4 DNA Ligase (NEB, 400,000 cohesive end units/ml), distilled water supplemented to 20 μL; they reacted at room temperature for 2 hours to obtain the ligation product, which was transferred into Trans10 competent cells and verified by sequencing, and thus plasmids pRS313-HIS3-$P_{TEF1}$-STpG-MAS-$T_{CYC1}$ and pRS425-LEU2-$P_{TEF1}$-STpGMAS-$T_{CYC1}$ were obtained.

Using plasmid pRS313-HIS3-$P_{TEF1}$-STpGMAS-$T_{CYC1}$ as a template, 6692 bp of plasmid pRS313-TEF1-STpGMAS-CYC1 backbone was amplified by using the primers in Table 3.

Using pRS425 as a template, LEU2 (1808 bp) was amplified by using the primers in Table 3.

The amplification system included: 5×Phusion HF Buffer 10 μL, dNTP (10 mM each dNTP) 1 μL, DNA template 20 ng, primers (10 μM) 1.5 μL for each, Phusion High-Fidelity DNA Polymerase (2.5 U/μL) 0.5 μL, and distilled water supplemented to a total volume of 50 μL. The amplification conditions were: pre-denaturation at 98° C. for 3 min (1 cycle); denaturation at 98° C. for 10 sec, annealing at 58° C. for 10 sec, extension at 72° C. for 4 min (30 cycles); and extension at 72° C. for 10 min (1 cycle).

The target fragment was purified from gel. 2 μL of 10×T4 DNA Ligase Reaction Buffer (NEB) and 1 μL of T4 Poly-nucleotide kinase (NEB) were added into the product of LEU2 fragment, and distilled water was supplemented to a total volume of 20 μL. A phosphorylation was performed at 37° C. for 1 h, and it was ligated to pRS313-P$_{TEF1}$-STpG-MAS-T$_{CYC1}$ by T4 DNA ligase (NEB) after being recovered from gel, transformed, and verified by sequencing to obtain plasmid pRS313-LEU2-P$_{TEF1}$-STpGMAS-T$_{CYC1}$.

(5) Construction of Plasmid pRS425-LEU2-P$_{TEF1}$-SynSmFPS-GGGS (SEQ ID NO: 15)-STpGMAS-T$_{CYC1}$ Using pUC57-SynSmFPS and pUC57-STpGMAS as templates, 1080 bp of SynSmFPS-GGGS (SEQ ID NO: 15) and 1704 bp of GGGS (SEQ ID NO: 15)-STpGMAS were obtained by amplification using the primers in Table 4.

The amplification system included: 5×Phusion HF Buffer 10 μL, dNTP (10 mM each dNTP) 1 μL, DNA template 20 ng, primers (10 μM) 1.5 μL for each, Phusion High-Fidelity DNA Polymerase (2.5 U/L) 0.5 μL, and distilled water supplemented to a total volume of 50 μL. The amplification conditions were: pre-denaturation at 98° C. for 3 min (1 cycle); denaturation at 98° C. for 10 sec, annealing at 58° C. for 10 sec, extension at 72° C. for 1 min (30 cycles); extension at 72° C. for 10 min (1 cycle).

SynSmFPS-GGGS (SEQ ID NO: 15) and GGGS (SEQ ID NO: 15)-STpGMAS were used together as templates, and 2767 bp of SynSmFPS-GGGS (SEQ ID NO: 15)-STpGMAS fragment was obtained by amplification using the primers in Table 4 (SexA1-SynSmFPS and STpGMAS-Asc1).

The amplification system included: 5×Phusion HF Buffer 10 μL, dNTP (10 mM each dNTP) 1 μL, DNA templates SynSmFPS-GGGS (SEQ ID NO: 15) and GGGS (SEQ ID NO: 15)-STpGMAS 20 ng for each, primers (10 μM) 1.5 μL for each, Phusion High-Fidelity DNA Polymerase (2.5 U/L) 0.5 μL, and distilled water supplemented to a total volume of 50 μL. The amplification conditions were: pre-denaturation at 98° C. for 3 min (1 cycle); denaturation at 98° C. for 10 sec, annealing at 58° C. for 10 sec, extension at 72° C. for 2 min (30 cycles); extension at 72° C. for 10 min (1 cycle).

The amplification product was purified, and then enzyme digested with SexA1 and Asc1, and the target fragment SexA1-SynSmFPS-GGGS (SEQ ID NO: 15)-STpGMAS-Asc1 (2760 bp) was recovered from gel, and prepared to use.

The plasmid pRS425-LEU2-P$_{TEF1}$-STpGMAS-T$_{CYC1}$ constructed in the above item "(4)" was enzyme digested with SexA1 and Asc1, and the 7602 bp large fragment was recovered from gel, so as to obtain the vector pRS425-LEU2-P$_{TEF1}$- . . . -T$_{CYC1}$; 50 ng of each of the vectors pRS425-LEU2-P$_{TEF1}$- . . . -T$_{CYC1}$ and SexA1-SynSmFPS-GGGS (SEQ ID NO: 15)-STpGMAS-Asc1 was added into the ligation system including: 2 μL 10×T4 DNA Ligase Reaction Buffer (NEB), 1 μL T4 DNA Ligase (NEB, 400,000 cohesive end units/ml), and distilled water supplemented to 20 μL; they reacted at room temperature for 2 hours to obtain a ligation product which was transferred into Trans10 competent cells, the plasmid was extracted and verified by sequencing, and plasmid pRS425-LEU2-P$_{TEF1}$-SynSmFPS-GGGS (SEQ ID NO: 15)-STpGMAS-T$_{CYC1}$ was obtained.

TABLE 3

Primer sequences

| Gene fragment | Primer name | Primer sequence (5'→3') |
|---|---|---|
| TEF1-STpGMAS-CYC1 | Sac11-TEF1 | GCGCCGCGGAGTGATCCCCCACACACCATAGCTT (SEQ ID NO: 28) |
| | CYC1-Sac11 | GCGCCGCGGGCGCGTTGGCCGATTCATTAATGCA (SEQ ID NO: 33) |
| pRS313-TEF1-STpGMAS-CYC1 | V313-to-R | CTTTGCCTTCGTTTATCTTGC (SEQ ID NO: 38) |
| | V313-to-F | TATATGTATACCTATGAATGTCAG (SEQ ID NO: 39) |
| LEU2 | Bsp-Leu-F | TGGCgTCCGGATTAAGCAAGGATTTTCTTAACTTCTTC (SEQ ID NO: 40) |
| | Bsp-Leu-R | TGGCgTCCGGAGATGCGGTATTTTCTCCTTACGCA (SEQ ID NO: 41) |

TABLE 4

Primer sequences

| Gene fragment | Primer name | Primer sequence (5'→3') |
|---|---|---|
| SynSmFPS-GGGS (SEQ ID NO: 15) | SexA1-SynSmFPS | ACCTGGTAAAACAATGGCTAATTTGAATGGTGAATC (SEQ ID NO: 42) |
| | SynSmFPS-GGGS SEQ ID NO: 15) | TGCTGCCATAGAACCACCACCTTTTTGTCTTTTATAGATTTTACC (SEQ ID NO: 43) |
| GGGS (SEQ ID NO: 15)-STpGMAS | GGGS (SEQ ID NO: 5)-STpGMAS | GGTGGTGGTTCTATGGCAGCAGTACAAGCAACCAC (SEQ ID NO: 44) |
| | STpGMAS-Asc1 | GGCGCGCCTCAGACTGGCAAGGAATCTA (SEQ ID NO: 45) |
| SynSmFPS-GGGS (SEQ ID NO: 15)-STpGMAS | SexA1-SynSmFPS | ACCTGGTAAAACAATGGCTAATTTGAATGGTGAATC (SEQ ID NO: 42) |
| | STpGMAS-Asc1 | GGCGCGCCTCAGACTGGCAAGGAATCTA (SEQ ID NO: 45) |

(6) Construction of Plasmid pRS425-LEU2-P$_{MF1}$-SynSmFPS-GGGS (SEQ ID NO: 15)-STpGMAS-T$_{CYC1}$ MF1 obtained in the above "1. Preparation of target genes" and plasmid pRS425-LEU2-P$_{TEF1}$-SynSmFPS-GGGS (SEQ ID NO: 15)-STpGMAS-T$_{CYC1}$ constructed in the above item "(5)" were double enzyme digested by using BamH1 (purchased from TaKaRa) and SexA1, respectively. 814 bp target promoter gene MF1 and 9898 bp vector fragment pRS425-LEU2- . . . -SynSmFPS-GGGS (SEQ ID NO: 15)-STpGMAS-T$_{CYC1}$ were purified from gel and the two (50 ng for each) were added into a ligation system including: 20 μL 10×T4 DNA Ligase Reaction Buffer (NEB), 1 μL T4 DNA Ligase (NEB, 400,000 cohesive end units/ml), and distilled water supplemented to 20 μL; they reacted at room temperature for 2 hours to obtain the ligation product which was transformed into Trans10 competent cells, and the plasmid was extracted and verified by sequencing. The plasmid obtained accordant with the correct sequence was named as pRS425-LEU2-P$_{MF1}$-SynSmFPS-GGGS (SEQ ID NO: 15)-STpGMAS-T$_{CYC1}$.

(7) Construction of Plasmid pM2-ERG20-GGGS (SEQ ID NO: 15)-LsLTC2

Using ERG20-GGGS (SEQ ID NO: 15) and GGGS (SEQ ID NO: 15)-LsLTC2 together as templates, an ERG20-GGGS (SEQ ID NO: 15)-LsLTC2 fragment of about 2744 bp was obtained by amplification using the primers (SexA1-ERG20 and LsLTC2-Asc1) in Table 5.

The amplification system included: 5×Phusion HF Buffer 10 μL, dNTP (10 mM each dNTP) 1 μL, DNA templates ERG20-GGGS (SEQ ID NO: 15) and GGGS (SEQ ID NO: 15)-LsLTC2 20 ng for each, primers (10 μM) 1.5 μL for each, Phusion High-Fidelity DNA Polymerase (2.5 U/μL) 0.5 μL, and distilled water supplemented to a total volume of 50 μL. The amplification conditions were: pre-denaturation at 98° C. for 3 min (1 cycle); denaturation at 98° C. for 10 sec, annealing at 58° C. for 10 sec, extension at 72° C. for 2 min (30 cycles); and extension at 72° C. for 10 min (1 cycle).

The amplification product was purified, and then enzyme digested with SexA1 and Asc1, and the target fragment SexA1-ERG20-GGGS (SEQ ID NO: 15)-LsLTC2-Asc1 (about 2744 bp) was recovered from gel, and then ligated with the enzyme-digested plasmid vector pM2-tHMG1 backbone, so as to obtain the recombinant plasmid pM2-ERG20-GGGS (SEQ ID NO: 15)-LsLTC2.

TABLE 5

Primer sequences

| Gene fragment | Primer name | Primer sequence (5'→3') |
|---|---|---|
| ERG20-GGGS (SEQ ID NO: 15) | SEXA1-ERG20 | GCGACCWGGTAAAACAATGGCTTCAGAAAAAGAAATTAGGAG (SEQ ID NO: 34) |
| | ERG20-GGGS (SEQ ID NO: 15) | CTTTCCCATAGAACCACCACCCTATTTGCTTCTCTTGTAAACT TTG (SEQ ID NO: 35) |
| GGGS (SEQ ID NO: 15)-LsLTC2 | GGGS (SEQ ID NO: 15)-LsLTC2 | GGTGGTGGTTCTATGGCAGCAGTTGACACTAA (SEQ ID NO: 36) |
| | LSLTC2-ASC1 | GCGGGCGCGCCTTACATGGATACAGAACCAACAAAT (SEQ ID NO: 37) |
| ERG20-GGGS (SEQ ID NO: 15)-STPGMAS | SEXA1-ERG20 | GCGACCWGGTAAAACAATGGCTTCAGAAAAAGAAATTAGGAG (SEQ ID NO: 34) |
| | LSLTC2-ASC1 | GCGGGCGCGCCTTACATGGATACAGAACCAACAAAT (SEQ ID NO: 37) |

(8) Construction of Plasmid pEASY-NDT80-HIS3

Using NK2-SQ genomic DNA and pRS313 as templates, 1252 bp of NDT80 (SEQ ID NO: 13) and 1168 bp of HIS3 (SEQ ID NO: 14) were obtained by amplification using the primers in Table 6.

The amplification system included: 5×Phusion HF Buffer 10 μL, dNTP (10 mM each dNTP) 1 μL, DNA template 20 ng, primers (10 μM) 1.5 μL for each, Phusion High-Fidelity DNA Polymerase (2.5 U/μL) 0.5 μL, and distilled water supplemented to a total volume of 50 μL. The amplification conditions were: pre-denaturation at 98° C. for 3 min (1 cycle); denaturation at 98° C. for 10 sec, annealing at 58° C. for 10 sec, extension at 72° C. for 1 min (30 cycles); and extension at 72° C. for 10 min (1 cycle).

The amplification product NDT80 was cloned into pEASY-Blunt Simple cloning vector (pEASY cloning vector, Beijing TransGen Biotech Co., Ltd.), transformed into Trans10 competent cells, and the plasmid was extracted and verified by sequencing, and thus plasmid pEASY-NDT80 was obtained.

TABLE 6

Primers

| Gene fragment | Primer name | Template | Primer sequence (5'→3') |
|---|---|---|---|
| NDT80 | NDT80-up-PmeI | Genomic DNA NK2-SQ | GCGGTTTAAACGTTCGACCATATTGATGAAGAGTGGG TAGG (SEQ ID NO: 46) |
|  | NDT80-down |  | CTGTTCCATTGATTTCTTCTCTATTGTTATATC (SEQ ID NO: 47) |
| HIS3 | Bsp-HIS-F | pRS313 | TGGCGTCCGGATCGCGCGTTTCGGTGATGACGG (SEQ ID NO: 48) |
|  | PmeI-HIS-R |  | GCGGTTTAAACGTGTCACTACATAAGAACACCT (SEQ ID NO: 49) | pEASY-NDT80 was enzyme digested by using PmeI (purchased from NEB (Beijing) Co., Ltd.), and 5122 bp target fragment (30 ng) was purified from gel, 4 L NEB buffer (reaction buffer, purchased from NEB (Beijing) Co., Ltd.) and t L CIP dephosphorylation enzyme (NEB) were added, and distilled water was supplemented to 40 µL; it was treated at 37° C. for 1 h, to which EDTA at a final concentration of 100 µmol was added, and it was kept at 6501 for 30 min to terminate the reaction. 5122 bp target fragment pEASY-NDT80 was recovered from gel, and prepared to use. HIS3 (30 ng) was purified from gel, 40 µL of 10×T4 DNA Ligase Reaction Buffer (NEB) and 1 µL of T4 Polynucleotide kinase (NEB) were added, and distilled water was supplemented to 400 µL, and it was phosphorylated at 3701 for 1 h. After being recovered from gel, it was ligated with pEASY-NDT80 by using T4 DNA ligase (NEB), transformed into Trans10 competent cells, and verified by sequencing to obtain plasmid pEASY-NDT80-HIS3.

The information of plasmids constructed above was shown in Table 7 below:

TABLE 7

Plasmid Information

| Plasmid name | Basic information |
|---|---|
| pM2-ADH2 | Containing $P_{PGK1}$-ADH2-$T_{ADH1}$ cassette |
| pM4-ACS1 | Containing $P_{TDH3}$-ACS1-$T_{TPI1}$ cassette |
| pM3-ALD6 | Containing $P_{TEF1}$-ALD6-$T_{CYC1}$ cassette |
| pRS313-LEU2-$P_{TEF1}$-STpGMAS-$T_{CYC1}$ | Containing $P_{TEF1}$-SynSmFPS-$T_{CYC1}$ cassette, LEU2, low-copy plasmid |
| pRS425-LEU2-$P_{TEF1}$-STpGMAS-$T_{CYC1}$ | Containing $P_{TEF1}$-SynSmFPS-$T_{CYC1}$ cassette, LEU2, high-copy plasmid |
| pRS425-LEU2-$P_{TEF1}$-SynSmFPS-GGGS (SEQ ID NO: 15)-STpGMAS-$T_{CYC1}$ | Containing $P_{TEF1}$-SynSmFPS-GGGS (SEQ ID NO: 15)-STpGMAS-$T_{CYC1}$ cassette, LEU2, high-copy plasmid |
| pRS425-LEU2-$P_{MF1}$-SynSmFPS-GGGS (SEQ ID NO: 15)-STpGMAS-$T_{CYC1}$ | Containing $P_{MF1}$-SynSmFPS-GGGS (SEQ ID NO: 15)-STpGMAS-$T_{CYC1}$ cassette, LEU2, high-copy plasmid |
| pEASY-NDT80-HIS3 | NDT80, HIS3 |

(9) Construction of Plasmid pEASY-rDNA-TRP1

Using NK2-SQ genomic DNA and pRS314 (Sikorski, R. S. and Hieter, P. 1989 Genetics 122(1): 19-27) as templates, respectively, rDNA (SEQ ID NO: 9) and TRP1 (SEQ ID NO: 10) were obtained by amplification using the primers in Table 8.

The amplification system included: 5×Phusion HF Buffer TL, dNTP (10 mM each dNTP) 1 µL, DNA template 20 ng, primers (10 µM) 1.5 µL for each, Phusion High-Fidelity DNA Polymerase (2.5 U/µL) 0.5 µL, and distilled water supplemented to a total volume of 50 µL. The amplification conditions were: pre-denaturation at 980° C. for 3 min (1 cycle); denaturation at 9801 for 10 sec, annealing at 58° C. for 10 sec, extension at 72° C. for 1 min (30 cycles); and extension at 72° C. for 10 min (1 cycle).

The amplification product rDNA was cloned into pEASY-Blunt Simple cloning vector and transformed into Trans10 competent cells, and the plasmid was extracted and verified by sequencing, so as to obtain plasmid pEASY-rDNA.

TABLE 8

Primers

| Gene fragment | Primer name | Template | Primer sequence (5'→3') |
|---|---|---|---|
| rDNA | rDNA-up-F | Genomic DNA of NK2-SQ | ATGAGAGTAGCAAACGTAAGTCT (SEQ ID NO: 50) |
| | rDNA-R-PmeI | | GCGGTTTAAACTTTCCTCTAATCAGGTTCCACCA (SEQ ID NO: 51) |
| TRP1 | BSP-TRP1-F | pRS314 | TGGCGTCCGGATACAATCTTGATCCGGAGCT (SEQ ID NO: 52) |
| | BSP-TRP1-R | | TGGCGTCCGGACACAAACAATACTTAAATAAATAC (SEQ ID NO: 53) | pEASY-rDNA was enzyme digested by using PmeI, and 5122 bp target fragment (30 ng) was purified from gel, 4 μL NEB buffer and 1 μL CIP dephosphorylation enzyme (NEB) was added, and distilled water supplemented to a total volume of 40 μL; it was treated at 37° C. for 1 h, to which EDTA at a final concentration of 10 μmol was added, and it was kept at 65° C. for 30 min to terminate the reaction. 5122 bp target fragment pEASY-rDNA was recovered from gel, and prepared to use.

TRP1 (30 ng) was purified from gel, 4 μL of 10×T4 DNA Ligase Reaction Buffer (NEB) and 1 μL of T4 Polynucleotide kinase (NEB) were added, and distilled water was supplemented to a total volume of 40 μL, and it was phosphorylated at 37° C. for 1 h. After being recovered from gel, it was ligated with pEASY-rDNA by using T4 DNA ligase (NEB), transformed into Trans10 competent cells, and verified by sequencing, and thus plasmid pEASY-rDNA-TRP1 was obtained.

Example 2: Construction of Recombinant Strains

1. Preparation of Yeast Competent Cells

The original strains were respectively cultured in the corresponding medium (Table 13) at 30° C., 250 rpm overnight. 1 mL of the culture suspension (with OD around 0.6-10) was added into a 1.5 mL EP tube, centrifuged at 10,000 g for 1 min under 4° C.; the resulted supernatant was discarded, the precipitate was washed with sterile water (4° C.) and centrifuged under the same conditions; and the resulted supernatant was discarded. 1 mL of a treatment solution (10 mM LiAc (lithium acetate); 10 mM DTT (dithiothreitol); 0.6M sorbitol; 10 mM Tris-HCl (tris(hydroxymethyl)aminomethane hydrochloride buffer, pH7.5), DTT was added immediately before using the treatment solution) was added into the yeast, and it was kept at 25° C. for 20 min. After centrifugation, the supernatant was discarded, and 1 mL of 1M sorbitol (filtered and sterilized through a 0.22 μm aqueous membrane) was added to re-suspend the yeast, then it was centrifuged, and the supernatant was discarded (re-suspended twice with 1M sorbitol) until the final volume became about 90 μL.

2. Construction of Strain FPP-001

1) Preparation of NDT80-HIS3-up, $P_{PGK1}$-ADH2-$T_{ADH1}$, $P_{TDH3}$-ACS1-$T_{TPI1}$, $P_{TEF1}$-ALD6-$T_{CYC1}$ and NDT80-HIS3-Down $P_{PGK1}$-ADH2-$T_{ADH1}$, $P_{TDH3}$-ACS1-$T_{TPI1}$, and $P_{TEF1}$-ALD6-$T_{CYC1}$ were expression cassettes carrying alcohol dehydrogenase 2, acetyl-CoA synthetase 1, and acetaldehyde dehydrogenase 6, respectively; NDT80-HIS3-up and NDT80-HIS3-down were the upstream and downstream homology arms of HIS3, respectively; the fragments were respectively amplified according to the following methods:

The functional modules were obtained by PCR using the templates and primers of PCR described in Table 9, respectively: 698 bp M1 (NDT80-HIS3-up), 2081 bp M2 ($P_{PGK1}$-ADH2-$T_{ADH1}$), 3519 bp M3 ($P_{TDH3}$-ACS1-$T_{TPI1}$), 2376 bp M4 ($P_{TEF1}$-ALD6-$T_{CYC1}$), 1835 bp M5 (NDT80-HIS3-down).

The amplification system included: 5×Phusion HF Buffer 10 μL, dNTP (10 mM each dNTP) 1 μL, DNA template 20 ng, primers (1 μM) 1.5 μL for each, Phusion High-Fidelity DNA Polymerase (2.5 U/μL) 0.5 μL, and distilled water supplemented to a total volume of 50 μL. The amplification conditions were: pre-denaturation at 98° C. for 3 min (1 cycle); denaturation at 98° C. for 10 sec, annealing at 58° C. for 10 sec, extension at 72° C. for 2 min (30 cycles); extension at 72° C. for 10 min (1 Cycle). The product was recovered from gel and stored.

TABLE 9

Primers

| Module | PCR template | Amplification fragment name | Primer name | Primer sequence (5'→3') |
|---|---|---|---|---|
| M1 | pEASY-NDT80-HIS3 | NDT80-HIS3-up | X1-M-pEASY-r-t-F | CTTGCAAATGCCTATTGTGCAGATGTTATAATATCTGTGCGTTTAATTAAGGCTCGTATGTTGTGTGGAATTGT (SEQ ID NO: 54) |
| | | | NDT80-interg-2 | CTGGCTTTAAAAAATGGATAAAAGGGATG (SEQ ID NO: 55) |
| M2 | pM2-ADH2 | $P_{PGK1}$-ADH2-$T_{ADH1}$ | 1-M-pEASY-PGK1-F | CTGTTTCCTGTGTGAAATTGTTATCCGCTCACAATTCCACACAACATACGAGCC |

TABLE 9-continued

Primers

| Module | PCR template | Amplification fragment name | Primer name | Primer sequence (5'→3') |
|---|---|---|---|---|
| | | | | TTAATTAAACGCACAGAT ATTATAAC (SEQ ID NO: 56) |
| | | | 3G-1-M-ADHt-TDH3-R | CCTCCGCGTCATTAAACT TCTTGTTGTTGACGCTAA CATTCAACGCTAGTATTC GGCATGCCGGTAGAGGTG TGG (SEQ ID NO: 57) |
| M3 | pM4-ACS1 | $P_{TDE3}$-ACS1-$T_{TPI1}$ | 3G-3-M-ADHt-TDH3-F | CAGGTATAGCATGAGGTC GCTCTTATTGACCACACC TCTACCGGCATGCCGAAT ACTAGCGTTGAATGTTAG CGTC (SEQ ID NO: 58) |
| | | | 3G-3-M-TPI1t-TEF1-R | AGGAGTAGAAACATTTTG AAGCTATGGTGTGTGGGG GATCACTTTAATTAATCT ATATAACAGTTGAAATTT GGA (SEQ ID NO: 59) |
| M4 | pM3-ALD6 | $P_{TEF1}$-ALD6-$T_{CYC1}$ | 3G-2-M-TPI1t-TEF1-F | GTCATTTTCGCGTTGAGA AGATGTTCTTATCCAAAT TTCAACTGTTATATAGAT TAATTAAAGTGATCCCCC ACAC (SEQ ID NO: 60) |
| | | | M-CYC1-pEASY-R | CGTATTACAATTCACTGG CCGTCGTTTTACAACGTC GTGACTGGGAAAACCCTG GCGCGTTGGCCGATTCAT TAATGC (SEQ ID NO: 61) |
| M5 | pEASY-NDT80-HIS3 | NDT80-HIS3-down | NDT80-interg-1 | CATCATAAGGAATTCCGG GATTCTCCCCAT (SEQ ID NO: 62) |
| | | | X2-M-pEASY-r-t-R | CGAAGGCTTTAATTTGCA AGCTGCGGCCCTGCATTA ATGAATCGGCCAACGCGC CAGGGTTTTCCCAGTCAC GACGTTG (SEQ ID NO: 63) |

2) Construction of Strain FPP-001

Original strain *Saccharomyces cerevisiae* NK2-SQ was cultured in a SD-Ura liquid medium (0.8% yeast selective medium SD-Ura-Trp-His (Beijing FunGenome Technology Co., Ltd.), 2% glucose, 0.005% His, 0.01% Trp) overnight, followed by being prepared into competent cells. Then, the transformation fragments M1, M2, M3, M4 and M5 in Table 9 were added in a total amount of 5 μg (molar ratio=1:1:1:1:1), mixed well and transferred to an electric shock cup, electrically shocked at 2.7 kv for 5.7 ms, to which 1 mL of 1M sorbitol was added, and it was resuscitated at 30° C. for 1 h, and spread onto a SD-Ura-His medium and cultured at 30° C. for 36 h or more. The ingredients in the screening medium composition were: 0.8% yeast selective medium SD-Ura-Trp-His (Beijing FunGenome Technology Co., Ltd.), 2% glucose, and 0.01% Trp. The true positive clone was identified by PCR, and named as strain FPP-001.

3 Construction of Strains ELE-001 and ELE-002

Original strain *Saccharomyces cerevisiae* FPP-001 was cultured in a SD-Ura-His liquid medium overnight, followed by being prepared into competent cells. Then, plasmids pRS313-LEU2-$P_{TEF1}$-STpGMAS-$T_{CYC1}$ and pRS425-LEU2-$P_{TEF1}$-STpGMAS-$T_{CYC1}$ were respectively added, mixed well and transferred into an electric shock cup, electrically shocked at 2.7 kv for 5.7 ms, to which 1 mL of 1M sorbitol was added, and it was resuscitated at 30° C. for 1 h, and spread onto a SD-Ura-His-Leu medium and cultured at 30° C. for 36 h or more. The ingredients in the screening medium composition were: 0.8% yeast selective medium SD-Ura-Trp-His (Beijing FunGenome Technology Co., Ltd.), 2% glucose, and 0.01% Trp. The true positive clone was identified by PCR, and named as strains ELE-001 (into which plasmid pRS313-LEU2-$P_{TEF1}$-STpGMAS-$T_{CYC1}$ was transferred) and ELE-002 (into which plasmid pRS425-LEU2-$P_{TEF1}$-STpGMAS-$T_{CYC1}$ was transferred), respectively.

4 Construction of Strain ELE-011

FPP-001 competent cells were prepared according to the steps in the above item 3. Then, plasmid pRS425-LEU2-$P_{TEF1}$-SynSmFPS-GGGS (SEQ ID NO: 15)-STpGMAS-$T_{CYC1}$ was added thereto, mixed well and transferred into an electric shock cup, electrically shocked at 2.7 kv for 5.7 ms, to which 1 mL of 1M sorbitol was added, and it was resuscitated at 30° C. for 1 h, and spread onto a SD-Ura-His-Leu medium and cultured at 30° C. for 36 h or more. The true positive clone was identified by PCR, and named as strain ELE-011.

5 Construction of Strains ELE-012 to ELE-019

Using plasmid pRS425-LEU2-$P_{TEF1}$-SynSmFPS-GGGS (SEQ ID NO: 15)-STpGMAS-$T_{CYC1}$ as a template, PCR amplification was performed by using the primers of Table 11 to obtain the amplification products corresponding to different primers. Then, the amplification products corresponding to different primers were respectively transferred into yeast FPP-001 for carrying out its own homologous recombination, and recombinant strains ELE-012 to ELE-018 were obtained, respectively. The linker peptide GGGS (SEQ ID NO: 15) of the fusion protein SynSmFPS-GGGS (SEQ ID NO: 15)-STpGMAS in the vector were replaced with 3A001, 4A001, 5A002, 6A005, 6B004, 8A005, 12A003, respectively (as shown in Table 10).

Using plasmid pRS425-LEU2-$P_{MF1}$-SynSmFPS-GGGS (SEQ ID NO: 15)-STpGMAS-$T_{CYC1}$ as a template, PCR amplification was performed by using the primers with the linker peptide of 8A005 in Table 10 (Table 11) to obtain the amplification products corresponding to different primers. Then, the amplification products corresponding to the different primers were respectively transferred into yeast FPP-001 for carrying out its own homologous recombination, and recombinant strain ELE-019 was obtained. The linker peptide GGGS (SEQ ID NO: 15) of the fusion protein SynSmFPS-GGGS (SEQ ID NO: 15)-STpGMAS in the vector was replaced with 8A005.

Table 10 Showing the Nucleotide Sequences and Amino Acid Sequences of Linker Peptides

| Linker peptide name | Nucleotide sequence (5'→3') | Amino acid sequence of linker peptide |
|---|---|---|
| 3A001 | TACGGTCAG | YGQ |
| 4A001 | CCGGGGGGACAC (SEQ ID NO: 64) | PGGH (SEQ ID NO: 16) |
| 5A002 | TATAGAAGTCAAATC (SEQ ID NO: 65) | YRSQI (SEQ ID NO: 17) |
| 6A005 | GTGATACCTTTTATTTCA (SEQ ID NO: 66) | VIPFIS (SEQ ID NO: 18) |
| 6B004 | TTTTTGTATCTTAAGTTT (SEQ ID NO: 67) | FLYLKF (SEQ ID NO: 19) |
| 8A005 | TGGCGGTTCTCGCCGAAGCTTCAG (SEQ ID NO: 68) | WRFSPKLQ (SEQ ID NO: 20) |
| 12A003 | CACCACGTGCAGGAGTCACAATGTATTTCCACAGTG (SEQ ID NO: 69) | HHVQESQCISTV (SEQ ID NO: 21) |

The specific reaction conditions were as follows:

The above amplification system included: 5×Phusion HF Buffer 10 μL, dNTP (10 mM each dNTP) 1 μL, DNA template 20 ng, primers (as shown in Table 11) (10 μM) 1.5 μL for each, Phusion High-Fidelity DNA Polymerase (2.5 U/L) 0.5 μL, and distilled water supplemented to a total volume of 50 μL. The amplification conditions were: pre-denaturation at 98° C. for 3 min (1 cycle); denaturation at 98° C. for 10 sec, annealing at 58° C. for 10 sec, extension at 72° C. for 5.5 min (30 cycles); extension at 72° C. for 10 min (1 cycle).

The amplification product was digested by using DpnI enzyme from Fermentas Company after being purified. The system thereof included: 5× Fast Digest Green Buffer 4 μL, purified product 34 μL, DpnI 2 μL. The enzyme digestion temperature and reaction time were 37° C. and 1 h, respectively. Finally, it was recovered from gel and stored.

TABLE 11

| | | Primers |
|---|---|---|
| Linker peptide | Primer name | Primer sequence (5'→3') |
| 3A001 | 50 bp-3A001-STpGmA | CAAGCAGTTTTGAAATCATTTTTGGGTAAAATCTATAAAAGACAAAAATACGGTCAGATGGCAGCAGTACAAGCAACCAC (SEQ ID NO: 70) |
| | SynSmFPS-Linker-R | TTTTTGTCTTTTATAGATTTTACC (SEQ ID NO: 71) |
| 4A001 | 50 bp-4A001-STpGmA | CAAGCAGTTTTGAAATCATTTTTGGGTAAAATCTATAAAAGACAAAACCGGGGGGACACATGGCAGCAGTACAAGCAACCAC(SEQ ID NO: 72) |
| | SynSmFPS-Linker-R | TTTTTGTCTTTTATAGATTTTACC (SEQ ID NO: 71) |
| 5A002 | 50 bp-5A002-STpGmA | CAAGCAGTTTTGAAATCATTTTTGGGTAAAATCTATAAAAGACAAAATATAGAAGTCAAATCATGGCAGCAGTACAAGCAACCAC(SEQ ID NO: 73) |
| | SynSmFPS-Linker-R | TTTTTGTCTTTTATAGATTTTACC (SEQ ID NO: 71) |
| 6A005 | 50 bp-6A005-STpGmA | CAAGCAGTTTTGAAATCATTTTTGGGTAAAATCTATAAAAGACAAAAGTGATACCTTTTATTTCAATGGCAGCAGTACAAGCAACCAC(SEQ ID NO: 74) |
| | SynSmFPS-Linker-R | TTTTTGTCTTTTATAGATTTTACC (SEQ ID NO: 71) |

TABLE 11-continued

Primers

| Linker peptide | Primer name | Primer sequence (5'→3') |
|---|---|---|
| 6B004 | 50 bp-6B004-STpGmA | CAAGCAGTTTTGAAATCATTTTTGGGTAAAATCTATAAAAGACAAAAATTTTTG TATCTTAAGTTTATGGCAGCAGTACAAGCAACCAC (SEQ ID NO: 75) |
| | SynSmFPS-Linker-R | TTTTTGTCTTTTATAGATTTTACC (SEQ ID NO: 71) |
| 8A005 | 50 bp-8A005-STpGmA | CAAGCAGTTTTGAAATCATTTTTGGGTAAAATCTATAAAAGACAAAAATGGCGG TTCTCGCCGAAGCTTCAGATGGCAGCAGTACAAGCAACCAC (SEQ ID NO: 76) |
| | SynSmFPS-Linker-R | TTTTTGTCTTTTATAGATTTTACC (SEQ ID NO: 71) |
| 12A003 | 50 bp-12A003-STpGmA | CAAGCAGTTTTGAAATCATTTTTGGGTAAAATCTATAAAAGACAAAAACACCAC GTGCAGGAGTCACAATGTATTTCCACAGTGATGGCAGCAGTACAAGCAACCAC (SEQ ID NO: 77) |
| | SynSmFPS-Linker-R | TTTTTGTCTTTTATAGATTTTACC (SEQ ID NO: 71) |

FPP-001 competent cells were prepared according to the steps in above item 3. Then, the products recovered from gel obtained in the previous step were respectively added thereto, mixed well and transferred into an electric shock cup, electrically shocked at 2.7 kv for 5.7 ms, to which 1 mL of 1M sorbitol was added, and it was resuscitated at 30° C. for 1 h, and respectively spread onto SD-Ura-His-Leu medium and cultured at 30° C. for 36 h or more. The true positive clone was identified by PCR, and named as strains ELE-012 to ELE-019, respectively.

6 Construction of Recombinant Strain ELE-020

1) Preparation of $P_{PGK}$-ERG20-GGGS (SEQ ID NO: 15)-LsLTC2-$T_{ADH1}$, $P_{TEF1}$-SynSmFPS-GGGS (SEQ ID NO: 15)-STpGMAS-$T_{CYC1}$, rDNA-TRP1-Up, and rDNA-TRP1-Down $P_{PGK}$-ERG20-GGGS (SEQ ID NO: 15)-LsLTC2-$T_{ADH1}$ and $P_{TEF1}$-SynSmFPS-GGGS (SEQ ID NO: 15)-STpG-MAS-$T_{CYC1}$ were expression cassette carrying a fusion protein of yeast farnesyl pyrophosphate synthase and lettuce-derived germacrene A synthetase, and a fusion protein of codon-optimized *Salvia miltiorrhiza*-derived farnesyl pyrophosphate synthase and codon-optimized *Tanacetum parthenium*-derived germacrene A synthetase, respectively; and rDNA-TRP1-up and rDNA-TRP1-down were the upstream and downstream homologous arms of rDNA, respectively; the fragments were amplified according to the following methods:

The functional modules were obtained by PCR using templates and primers described in Table 12, respectively:

M1 (rDNA-TRP1-up), (SEQ ID NO: 15)
M2 ($P_{PGK1}$-ERG20-GGGS-LsLTC2-$T_{ADH1}$), (SEQ ID NO: 15)
M3 ($P_{TEF1}$-SynSmFPS-GGGS-STpGMAS-$T_{CYC1}$),

M4 (rDNA-TRP1-down).

The amplification system included: 5×Phusion HF Buffer 10 μL, dNTP (10 mM each dNTP) 1 μL, DNA template 20 ng, primers (10 μM) 1.5 μL for each, Phusion High-Fidelity DNA Polymerase (2.5 U/μL) 0.5 μL, and distilled water supplemented to a total volume of 50 μL. The amplification conditions were: pre-denaturation at 98° C. for 3 min (1 cycle); denaturation at 98° C. for 10 sec, annealing at 58° C. for 10 sec, extension at 72° C. for 2 min (30 cycles); and extension at 72° C. for 10 min (1 cycle). The product was recovered from gel and stored.

TABLE 12

Primers

| Module | PCR template | Amplification fragment name | Primer name | Primer sequence (5'→3') |
|---|---|---|---|---|
| M1 | pEASY-rDNA-TRP1 | rDNA-TRP1-up | X1-M-pEASY-r-t-F | CTTGCAAATGCCTATTGTG CAGATGTTATAATATCTGT GCGTTTAATTAAGGCTCGT ATGTTGTGTGGAATTGT (SEEQ ID NO: 54) |
| | | | X1-r-t-R-rDNA | CTCACTATTTTTTACTGCG GAAGCGG (SEEQ ID NO: 78) |
| M2 | pM2-ERG20-GGGS (SEQ ID NO: 15)-LsLTC2 | $P_{PGK1}$-ERG20-GGGS (SEQ ID NO: 15)-LTC2-$T_{ADH1}$ | 1-M-pEASY-PGK1-F | CTGTTTCCTGTGTGAAATT GTTATCCGCTCACAATTCC ACACAACATACGAGCCTT AATTAAACGCACAGATATT ATAAC (SEQ ID NO: 56) |
| | | | 1-M-ADHt-TEF1-R | GGAGTAGAAACATTTTGAA GCTATGGTGTGTGGGGGA TCACTTTAATTAATCGGCA |

TABLE 12-continued

Primers

| Module | PCR template | Amplification fragment name | Primer name | Primer sequence (5'→3') |
|---|---|---|---|---|
| | | | | TGCCGGTAGAGGTG (SEEQ ID NO: 79) |
| M3 | pRS425-LEU2-P$_{TEF1}$-SynSmFPS-GGGS (SEQ ID NO: 15)-STpGMAS-T$_{CYC1}$ | P$_{TEF1}$-SynSmFPS-GGGS (SEQ ID NO: 15)-STpGMAS-T$_{CYC1}$ | 2-M-ADHt-TEF1-F | GGTATAGCATGAGGTCGC TCTTATTGACCACACCTCT ACCGGCATGCCGATTAATT AAAGTGATCCCCCA (SEEQ ID NO: 80) |
| | | | M-CYC1-pEASY-R | CGTATTACAATTCACTGGC CGTCGTTTTACAACGTCGT GACTGGGAAAACCCTGGC GCGTTGGCCGATTCATTAA TGC (SEEQ ID NO: 61) |
| M4 | pEASY-rDNA-TRP1 | rDNA-TRP1-down | X2-r-t-F-rDNA | GAACTGGGTTACCCGGGG CACCTGTC (SEEQ ID NO: 81) |
| | | | X2-M-pEASY-r-t-R | CGAAGGCTTTAATTTGCAA GCTGCGGCCCTGCATTAA TGAATCGGCCAACGCGCC AGGGTTTTCCCAGTCACG ACGTTG (SEEQ ID NO: 63) |

Original strain *Saccharomyces cerevisae* ELE-019 was cultured in a SD-Ura-His-Leu liquid medium overnight, followed by being prepared into competent cells. Then, the transformation fragments M1, M2, M3, and M4 in Table 12 were added in a total amount of 40 μg (molar ratio=1:1:1:1), mixed well and transferred into an electric shock cup, electrically shocked at 2.7 kv for 5.7 ms, to which 1 mL of 1M sorbitol was added, and it was resuscitated at 30 for 1 h, and spread onto SD-Ura-His-Leu-Trp medium and cultured at 300 h for 36 h or more. The ingredients in the screening medium composition were: 0.8% yeast selective medium SD-Ura-His-Leu-Trp (Beijing FunGenome Technology Co., Ltd.), 2% glucose. The true positive clone was identified by PCR, and named as strain ELE-020.

This ELE-020 recombinant strain was deposited on Oct. 20, 2017 at the China General Microbiological Culture Collection Center, CGMCC. The deposition address was Building 3, No. 1 West Beichen Road, Chaoyang District, Beijing. The strain name was: *Saccharomyces cerevisae*, the latin name thereof is: *Saccharomyces cerevisiae*; and the deposition number thereof was: CGMCC No. 14829.

The information of all the above engineering strains was shown in Table 13.

TABLE 13

Information of engineering strains

| Strain name | Basic information | Medium |
|---|---|---|
| NK2-SQ | P$_{PGK1}$-tHMG1-T$_{ADH1}$, P$_{PDC1}$-ERG12-T$_{ADH2}$, P$_{ENO2}$-IDI1-T$_{PDC1}$, P$_{PYK1}$-ERG19-T$_{PGI1}$, P$_{FBA1}$-ERG13-T$_{TDH2}$, P$_{TDH3}$-ERG8-T$_{TPI1}$ and P$_{TEF1}$-ERG10-T$_{CYC1}$ and the screening marker of URA3 were integrated into GAL7 site of the chromosome of strain CEN.PK2-1D (MATαura3-52, trp1-289, leu2-3, 112, his3Δ1; MAL2-8C, SUC2) | SD-Ura |
| FPP-001 | P$_{PGK1}$-ADH2-T$_{ADH1}$, P$_{TEF1}$-ALD6-T$_{CYC1}$, P$_{TDH3}$-ACS1-T$_{TPL1}$ and the screening marker of HIS3 were integrated into NDT80 site of the chromosome of strain NK2-SQ | SD-Ura-His |
| ELE-001 | FPP-001 transferred with pRS313-LEU2-P$_{TEF1}$-STpGMAS-T$_{CYC1}$ | SD-Ura-His-Leu |
| ELE-002 | FPP-001 transferred with pRS425-LEU2-P$_{TEF1}$-STpGMAS-T$_{CYC1}$ | SD-Ura-His-Leu |
| ELE-011 | FPP-001 transferred with pRS425-LEU2-P$_{TEF1}$-SynSmFPS-GGGS (SEQ ID NO: 15)-STpGMAS-T$_{CYC1}$ | SD-Ura-His-Leu |
| ELE-012 | FPP-001 transferred with pRS425-LEU2-P$_{TEF1}$-SynSmFPS-3A001-STpGMAS-T$_{CYC1}$ | SD-Ura-His-Leu |
| ELE-013 | FPP-001 transferred with pRS425-LEU2-P$_{TEF1}$-SynSmFPS-4A001-STpGMAS-T$_{CYC1}$ | SD-Ura-His-Leu |
| ELE-014 | FPP-001 transferred with pRS425-LEU2-P$_{TEF1}$-SynSmFPS-5A002-STpGMAS-T$_{CYC1}$ | SD-Ura-His-Leu |
| ELE-015 | FPP-001 transferred with pRS425-LEU2-P$_{TEF1}$-SynSmFPS-6A005-STpGMAS-T$_{CYC1}$ | SD-Ura-His-Leu |
| ELE-016 | FPP-001 transferred with pRS425-LEU2-P$_{TEF1}$-SynSmFPS-6B004-STpGMAS-T$_{CYC1}$ | SD-Ura-His-Leu |

TABLE 13-continued

Information of engineering strains

| Strain name | Basic information | Medium |
|---|---|---|
| ELE-017 | FPP-001 transferred with pRS425-LEU2-$P_{TEF1}$-SynSmFPS-8A005-STpGMAS-$T_{CYC1}$ | SD-Ura-His-Leu |
| ELE-018 | FPP-001 transferred with pRS425-LEU2-$P_{TEF1}$-SynSmFPS-12A003-STpGMAS-$T_{CYC1}$ | SD-Ura-His-Leu |
| ELE-019 | FPP-001 transferred with pRS425-LEU2-$P_{MF1}$-SynSmFPS-8A005-STpGMAS-$T_{CYC1}$ | SD-Ura-His-Leu |
| ELE-020 | $P_{PGK1}$-ERG20-GGGS (SEQ ID NO: 15)-LsLTC2-$T_{ADH1}$, $P_{TEF1}$-SynSmFPS-GGGS (SEQ ID NO: 15)-STpGMAS-$T_{CYC1}$ and the screening marker of TRP1 were integrated into the rDNA site of the chromosome of strain ELE-019 | SD-Ura-His-Leu-Trp |

Example 3: Application of Recombinant Strain in Producing β-Elemene

1. Engineering Strain Culture and Product Extraction

All engineering yeast strains prepared in Example 2 were activated in the corresponding solid selective medium SD-Ura-His-Leu, and seed solutions were prepared in the corresponding liquid selective medium SD-Ura-His-Leu (30° C., 250 rpm, 16 h), inoculated in an amount of 1% into a 100 mL trigonal flask containing 15 mL of the corresponding liquid selective medium, shaken at 250 rpm and cultured at 30° C. for 1 d. Then, 1.5 mL of n-dodecane was added thereto, and continued to be shaken and cultured for 5 d. Finally, the liquid in the trigonal flask was transferred to a 50 mL centrifuge tube, centrifuged at 5,000 rpm for 5 min, and the organic phase was collected for use.

2. β-Elemene Conversion and its Qualitative and Quantitative Analyses

1) β-Elemene Conversion

The above organic phase sample was heated in an oil bath at 100-380° C. (180° C.) within a fuming cupboard for 1 h to obtain a converted material.

2) Detection

Figure 2:
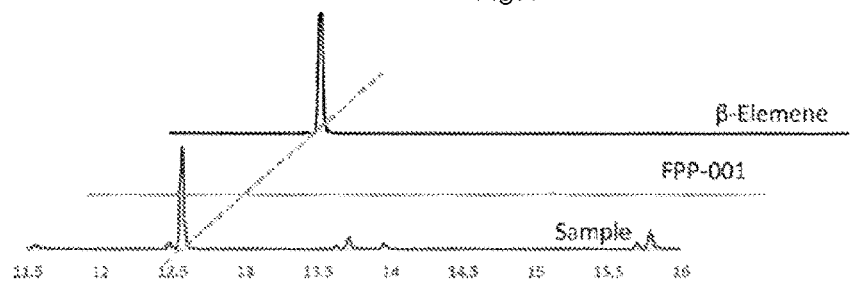
FIG. 2 is a GC-MS test chromatomap.
Figure 2:
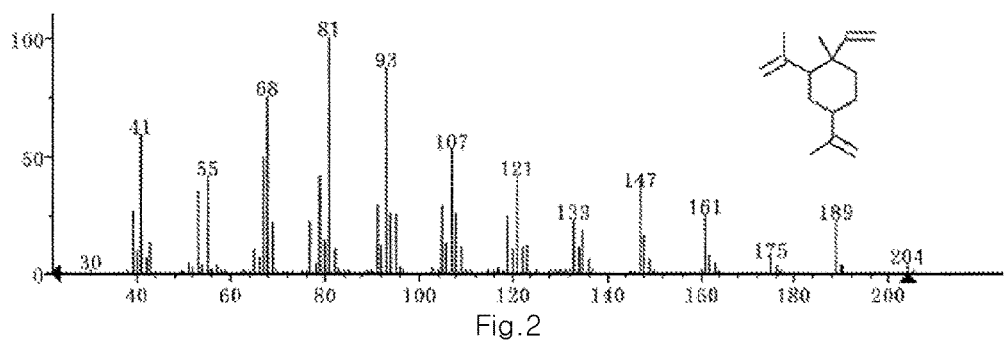

The converted material was diluted 10 times with n-hexane, filtered through an organic nylon membrane (0.22 μm), and detected by using GC-MS. Testing equipment: Agilent GCMSD Agilent 7890A/5975C; GC-MS measurement conditions: inlet temperature 250° C., injection volume 1 μL, splitless, solvent delay 3 min; column: HP-5 ms (30 m*0.25 mm); Chromatographic conditions: 45° C. for 1 min, warming up to 300° C. at 10° C./min and keeping for 5 min; MS conditions: Full Scan: 50-750 amu. Qualitative and quantitative analyses were carried out by using the standard of β-elemene, which was purchased from the China National Institutes for Food and Drug Control (Cat. No. 100268). FIG. 2 is a GC-MS test chromatomap of β-elemene produced by all engineering yeast strains prepared in Example 2.

As a result, the yield of each engineering strain after fermentation for 6 days was as follows:

Engineering strains ELE-001 and ELE-002 were obtained by introducing low and high copy number of STpGMAS based on FPP-001. Wherein, the yield of β-elemene of ELE-001 reached 9.3 mg/L, and the yield of β-elemene of ELE-002 reached 22.1 mg/L;

Engineering strain ELE-011 was obtained by introducing high copy number of fusion protein gene SynSmFPS-GGGS (SEQ ID NO: 15)-STpGMAS based on FPP-001, and the yield of β-elemene reached 101.1 mg/L.

Engineering strains ELE-012 to ELE-019 (the promoters and linkers thereof were TEF1 and 3A001, TEF1 and 4A001, TEF1 and 5A002, TEF1 and 6A005, TEF1 and 6B004, TEF1 and 8A005, TEF1 and 12A003, MF1 and 8A005, respectively) were obtained by introducing high copy number of fusion protein gene SynSmFPS-Linker-STpGMAS based on FPP-001.

Engineering strain ELE-020 was obtained by the recombination and introduction of fusion protein genes $P_{PGK1}$-ERG20-GGGS(SEQ ID NO: 15)-LsLTC2-$T_{ADH1}$, and $P_{TEF1}$-SynSmFPS-GGGS (SEQ ID NO: 15)-STpGMAS-$T_{CYC1}$, based on ELE-019.

The yields of β-elemene produced by using strains ELE-012 to ELE-020 were 2.2 mg/L (relative to the culture solution), 35.5 mg/L, 110.4 mg/L, 108.6 mg/L, 73.6 mg/L, 109.7 mg/L, 48.3 mg/L, 158.1 mg/L and 469 mg/L, respectively.

3. Bioreactor Fermentation Culture

1) Medium Formulation

The calcium chloride mother liquid: 19.2 g/L aqueous solution of calcium chloride dihydrate.

The trace metal salt mother liquid: 19.1 g/L of disodium ethylenediamine tetraacetate, 10.2 g/L of zinc sulfate heptahydrate, 0.5 g/L of manganese chloride tetrahydrate, 0.86 g/L of cobalt chloride hexahydrate, 0.78 g/L of copper sulfate pentahydrate, 0.56 g/L of sodium molybdate dehydrate, and 5.12 g/L of iron sulphite heptahydrate.

The vitamin mother liquid: 0.05 g/L of biotin, 0.2 g/L of sodium p-aminobenzoate, 1 g/L of niacin, 1 g/L of calcium pantothenate, 1 g/L pyridoxine hydrochloride, 1 g/L of thiamine hydrochloride, and 25 g/L of inositol.

The seed medium and the fermentation medium: 25 g/L of glucose, 15 g/L of ammonium sulfate, 6.15 g/L of magnesium sulfate heptahydrate, 0.72 g/L of zinc sulfate heptahydrate, 8 g/L of potassium dihydrogen phosphate, 2 mL/L of calcium chloride mother liquid, 10 mL/L of trace metal salt mother liquid; 12 mL/L of vitamin mother liquid, 1 g/L of tryptophan, and the balance of water.

The fed-batch medium: 800 g/L of glucose, 5.125 g/L of magnesium sulfate heptahydrate, 3.5 g/L of potassium sulfate, 0.28 g/L of sodium sulfate, 9 g/L of potassium dihydrogen phosphate, 1 g/L of tryptophan, and the balance of water.

2) Fermentation of Engineering Strain ELE-019

The engineering strain ELE-019 was activated according to the methods in item 1. The monoclonal colony on the plate was picked up and inoculated into a test tube containing SD-Ura-His-Leu medium, and shaken at 250 rpm and cultured at 30° C. overnight; 500 μL of the strain culture was pipetted into a 250 mL trigonal flask containing 50 mL of SD-Ura-His-Leu medium, and shaken at 250 rpm and cultured at 30° C. for 24 h.

2 mL of the strain culture was respectively pipetted into three 1 L trigonal flasks containing 100 mL of seed medium, shaken at 250 rpm and cultured at 30° C. for 48 h; finally, the seed solution was inoculated into a 7 L fermentation tank containing 3 L of the fermentation medium via a flame inoculation loop (Eppendorf Company, Germany, model no.: BioFlo®320).

The parameters set in the fermentation process were: temperature 30° C., pH 5.0, dissolved oxygen 30%, air flow rate 3-20 L/min, stirring speed 300-1000 rpm; and dissolved oxygen were cascading with stirring speed and air flowing. When the dissolved oxygen value was greater than 60%, the fed-batch medium was added into the fermentation tank until the glucose concentration in the fermentation liquid was 5 g/L.

Three hours before the end of the fermentation, 10% (relative to the volume of the culture solution) of n-dodecane was added, and after the end of the fermentation, the organic phase was separated.

After the treatment carried out according to the conversion and detection methods in item 2, qualitative and quantitative analyses were performed. After high-density fermentation of the engineering strain ELE-019 for 96 hours, 2 g/L (relative to the culture solution) of β-elemene may be obtained. The recombinant strains complying with the object of the present invention, including but not limited to the specific experimental examples described in Table 13, may be subjected to a fermentation culture according to the fermentation methods described in item "3" to obtain germacrene A.

INDUSTRIAL APPLICATION

The experiments of the present invention verified that a recombinant strain can be obtained by expressing germacrene A synthetase gene or fusion protein gene thereof in a host yeast in the present invention, which can greatly improve the yield of germacrene A. It is suitable for industrial production of β-elemene and/or germacrene A, and provides a potent strain and research basis for the biosynthesis of anti-cancer raw material β-elemene.

---

What is claimed is:

1. A recombinant yeast strain, comprising:
a fusion protein
comprising germacrene A synthetase and farnesyl pyrophosphate synthase, wherein the fusion protein is one or more selected from the group consisting of:
(1) SynSmFPS-GGGS (SEQ ID NO: 15)-STpGMAS,
(2) SynSmFPS-PGGH (SEQ ID NO: 16)-STpGMAS,
(3) SynSmFPS-YRSQI (SEQ ID NO: 17)-STpGMAS,
(4) SynSmFPS-VIPFIS (SEQ ID NO: 18)-STpGMAS,
(5) SynSmFPS-FLYLKF (SEQ ID NO: 19)-STpGMAS,
(6) SynSmFPS-WRFSPKLQ (SEQ ID NO: 20)-STpGMAS,
(7) SynSmFPS-HHVQESQCISTV (SEQ ID NO: 21)-STpGMAS, and
(8) a combination of SynSmFPS-WRFSPKLQ (SEQ ID NO: 20)-STpGMAS, ERG20-GGGS (SEQ ID NO: 15)-LsLTSC2 and SynSmFPS-GGGS (SEQ ID NO: 15)-STpGMAS.

2. The recombinant yeast strain of claim 1, wherein said recombinant yeast strain comprises said fusion protein, and said fusion protein is encoded by one or more nucleic acids encoding the germacrene A synthetase and one or more nucleic acids encoding the farnesyl pyrophosphate synthase.

3. The recombinant yeast strain of claim 2, wherein said fusion protein is encoded by at least two nucleic acids encoding the germacrene A synthetase and at least two nucleic acids encoding the farnesyl pyrophosphate synthase and, wherein the at least two nucleic acids encoding the germacrene A synthetase are different or the same, and the at least two nucleic acids encoding the farnesyl pyrophosphate synthase are different or the same.

4. The recombinant yeast strain of claim 2, wherein said germacrene A synthetase is encoded by:
a nucleic acid set forth in SEQ ID NO:3 or a nucleic acid set forth in positions 13-1686 of SEQ ID NO:12; and
said farnesyl pyrophosphate synthase is encoded by:
a nucleic acid set forth in SEQ ID NO:2 or a nucleic set forth in positions 1-1056 of SEQ ID NO: 11.

5. The recombinant yeast strain of claim 1, wherein said yeast strain comprises a nucleic acid encoding the fusion protein.

6. The recombinant yeast strain of claim 5, wherein the nucleic acid encoding the fusion protein is contained in an expression cassette.

7. The recombinant yeast strain of claim 6, wherein the expression cassette further comprises a promoter and a terminator.

8. The recombinant yeast strain of claim 7, wherein the promoter is selected from TEF1, MF1 or PGK1 and the terminator is CYC1 or ADH1.

9. The recombinant yeast strain of claim 1, wherein the recombinant yeast strain further expresses one or more marker genes.

10. The recombinant yeast strain of claim 9, wherein the marker gene is selected from his3 or trp1.

11. The recombinant yeast strain of claim 6, wherein the expression cassette is contained in a vector.

12. The recombinant yeast strain of claim 6, wherein the expression cassette is contained in a plasmid or is integrated into a chromosome of said yeast strain.

13. The recombinant yeast strain of claim 1, wherein said yeast strain comprises an increased copy number of a nucleic acid encoding an alcohol dehydrogenase, a nucleic acid encoding an acetaldehyde dehydrogenase and a nucleic acid encoding an acetyl-CoA synthetase, as compared to the original yeast prior to modification.

14. The recombinant yeast strain of claim 13, wherein said yeast strain comprises an expression cassette configured to increase the copy number of said nucleic acid encoding the alcohol dehydrogenase, an expression cassette configured to increase the copy number of said nucleic acid encoding the acetaldehyde dehydrogenase, an expression cassette configured to increase the copy number of said nucleic acid encoding the acetyl-CoA synthetase, and a marker gene introduced by homologous recombination.

15. The recombinant yeast strain of claim 1, wherein the original yeast is *Saccharomyces cerevisiae*.

16. The recombinant yeast strain of claim 15, wherein said *Saccharomyces cerevisiae* is *Saccharomyces cerevisiae* NK2-SQ.

17. The recombinant yeast strain of claim 15, wherein said recombinant yeast strain is *Saccharomyces cerevisiae* CGMCC No. 14829.

18. A method of producing germacrene A, comprising fermenting the recombinant yeast strain of claim 1 to obtain germacrene A.

19. A method of producing β-elemene, comprising:
(a) fermenting the recombinant yeast strain of claim 1 to obtain a fermentation product;
(b) extracting the fermentation product with an organic solvent, and collecting the organic phase; and
(c) heating the organic phase of step b to obtain β-elemene.

20. The method of claim 19, wherein the fermentation of step (a) comprises:

first, culturing the recombinant strain in a seed medium to obtain a seed liquid;

second, inoculating the seed liquid into a fermentation medium and conducting fermentation culture; and third, generating a product of the fermentation culture, which is named as a fermentation system.

21. The method of claim 20, wherein during the fermentation culture, a fed-batch medium is added into the fermentation system.

22. The method of claim 21, wherein when the dissolved oxygen value in the fermentation system is greater than 60%, a fed-batch medium is added into the fermentation system until glucose concentration in the fermentation system reaches 5 g/L.

23. The method of claim 20, wherein a formulation of the seed medium and the fermentation medium contains per L volume: 25 g of glucose, 15 g of ammonium sulfate, 6.15 g of magnesium sulfate heptahydrate, 0.72 g of zinc sulfate heptahydrate, 8 g of potassium dihydrogen phosphate, 2 mL of calcium chloride mother liquid, 10 mL of trace metal salt mother liquid; 12 mL of vitamin mother liquid, and 1 g of tryptophan, wherein the calcium chloride mother liquid is 19.2 g/L aqueous solution of calcium chloride dehydrate, wherein the trace metal salt mother liquid contains per L volume: 19.1 g of disodium ethylenediamine tetraacetate; 10.2 g of zinc sulfate heptahydrate; 0.5 g of manganese chloride tetrahydrate; 0.86 g of cobalt chloride hexahydrate; 0.78 g of copper sulfate pentahydrate; 0.56 g of sodium molybdate dihydrate; and 5.12 g of iron sulphite heptahydrate, wherein the vitamin mother liquid contains per L volume: 0.05 g of biotin; 0.2 g of sodium p-aminobenzoate; 1 g of niacin; 1 g of calcium pantothenate; 1 g pyridoxine hydrochloride; 1 g of thiamine hydrochloride; and 25 g of inositol.

24. The method of claim 21, wherein the fed-batch medium contains per L volume: 800 g of glucose, 5.125 g of magnesium sulfate heptahydrate, 3.5 g of potassium sulfate, 0.28 g of sodium sulfate, 9 g of potassium dihydrogen phosphate and 1 g of tryptophan.

25. The method of claim 19, wherein:
the organic solvent is n-dodecane; and
the heating is at 100-380° C. for 1 hour.

* * * * *

SEQUENCE LISTING

```
Sequence total quantity: 81
SEQ ID NO: 1            moltype = DNA   length = 808
FEATURE                 Location/Qualifiers
misc_feature            1..808
                        note = MF1
source                  1..808
                        mol_type = other DNA
                        organism = synthetic construct
SEQUENCE: 1
gggaagacat gcttaacaag aagatataat tatataatat atatattatt aataataaca   60
tccttactgc agtcctgttg tgggagaaaa tggagagaga ctatgtttcg tatcaattcc  120
taaaatcaaa aaaaaaaaaa aaaaaaagtt aaacaagcac tcgctgttca tttgttttac  180
aagtattcat actctaatag gtcattgagc ttcttttctt gaggagagat ccaatttgaa  240
gtcggaataa gatttgcttt cattagcgta ggcaataatt atgagataaa tggtgcagca  300
ctattaagta gtgtggattt caataatttc cgaattagga ataaatgcgc taaatagaca  360
tcccgttctc tttggtaatc tgcataattc tgatgcaata tccaacaact atttgtgcaa  420
ttatttaaca aaatccaatt aactttccta attagtcctt caatagaaca tctgtattcc  480
tttttttat gaacaccttc ctaattaggc catcaacgac agtaaatttt gccgaattta  540
atagcttcta ctgaaaaaca gtggaccatg tgaaagatg catctcattt atcaaacaca  600
taatattcaa gtgagcctta cttcaattgt attgaagtgc aagaaaacca aaaagcaaca  660
acaggttttg gataagtaca tatataagag ggcctttttgt tcccatcaaa aatgttactg  720
ttcttacgat tcatttacga ttcaagaata gttcaaacaa gaagattaca aactatcaat  780
ttcatacaca atataaacga ttaaaaga                                     808

SEQ ID NO: 2            moltype = DNA   length = 1071
FEATURE                 Location/Qualifiers
misc_feature            1..1071
                        note = Nucleic acid encoding the farnesyl pyrophosphate
                         synthase
source                  1..1071
                        mol_type = other DNA
                        organism = synthetic construct
SEQUENCE: 2
acctggtaaa acaatggcta atttgaatgg tgaatctgct gatttgagag caacattttt   60
gggtgtttac tctgttttga agtcagaatt gttgaatgat ccagcatttg aatggacaga  120
tggttcaaga caatgggttg aaagaatgtt ggattacaac gttccaggtg gtaaattgaa  180
cagaggtttg tctgttattg attcatacaa attgttgaag ggtggtaaag atttgactga  240
tgatgaagtt ttcttggctt ctgcattagg ttggtgtgtt gaatggttac aagcatactt  300
tttggttttg gatgatatca tggataactc acatacaaga agaggtcaac catgttggtt  360
tagagttcca aaagttggta tgatcgcaat taatgatggt atcatcttga gaaatcatat  420
tccaagaatt ttgaagaaac attttagaac taaaccatac tacgttgatt tgttggatt  480
gtttaatgaa gttgaattcc aaacagcttc tggtcaaatg atcgatttga tcactacaat  540
cgaaggtgaa aaggatttgt ctaagtactc attgccattg catagaagaa tcgttcaata  600
caagactgct tattactcat tttacttgcc agttgcttgt gcattgttaa tggcaggtga  660
agatttggaa aaacatccaa cagttaagga tgttttgatt aatatgggta tctatttcca  720
agttcaagat gattacttag attgttttgg tgaaccagaa aagattggta aaatcggtac  780
tgatatcgaa gatttcaagt gttcttggtt ggttgttaaa gcattggaat tgtgtaacga  840
agaacaaaag aaaactttat ttgaacatta tggtaaagaa gatccagctg atgttgcaaa  900
gattaaagtt ttgtacaacg aaattaattt gcaaggtgtt ttcgcagaat tcgaatctaa  960
gtcatacgaa aaattgaatt cttcaattga agctcatcca tctaagtcag ttcaagcagt 1020
```

```
tttgaaatca ttttttgggta aaatctataa aagacaaaaa taaggcgcgc c            1071

SEQ ID NO: 3              moltype = DNA  length = 1701
FEATURE                   Location/Qualifiers
misc_feature              1..1701
                          note = Nucleic acid encoding the germacrene A synthetase
source                    1..1701
                          mol_type = other DNA
                          organism = synthetic construct
SEQUENCE: 3
acctggtaaa acaatggcag cagtacaagc aaccacaggt attcaagcaa acacaaaaac   60
ttccgcagaa ccagtaagac cattagccaa tttcccacca tccgtttggg gtgacagatt   120
tttatccttc agtttggaca agagtgaatt cgaaagatac gctatcgcaa tggaaaagcc   180
aaaggaagat gttagaaagt taatcgttga ttctactatg gactcaaacg aaaaattggg   240
tttgatctat tccgttcata gagtcggttt gacatacatg ttcttgcaag aaatagaatc   300
ccaattggat aaaattgttta atgaattcag tttgcaagat tacgaagaag tagacttgta   360
cactatctca attaacttcc aagttttcag cacttaggt tacaaattgc cttgtgatgt    420
ttttaaaaag tttaaagacg ctatatccgg tacttttaaa gaatccataa ccagtgatgt   480
tagaggcatg ttgggtttgt acgaaagtgc tcaattgaga attagaggtg aaaagatatt   540
ggatgaagca tccgttttca ttgagggtaa attgaagagt gttgtcaaca cattggaggg   600
taacttggcc caacaagtca agcaatcatt aagaagacca ttccatcagg gtatgcctat   660
ggtagaagca agattgtatt tctctaacta cgaagaagaa tgctcttcac atgattcatt   720
gtttaaatta gcaaagttgc acttcaagta tttggaattg caacaaaagg aagaattgag   780
aatcgtcacc aagtggtaca aggatatgag attccaagaa actacaccat acatcagaga   840
cagagttcct gaaatctact tatggatttt gggtttgtac ttcgaaccaa gatactcttt   900
ggctagaata atcgcaacca agatcacttt gttcttagta gttttggatg acacttatga   960
tgcctacgct acaatcgaag aaatcagatt gttgaccgat gctataaata agtgggacat   1020
ttctgcaatg aacaaaatcc agaatacat cagaccttc tacaaggttt tgttggatga    1080
atacgctgaa ataggtaaaa gaatggcaaa ggaaggtaga gccgatactg ttatcgcctc   1140
taaagaagca tttcaagaca ttgcaagagg ttatttggaa gaagccgaat ggacaaactc   1200
tggttatgtt gcatcattcc cagaatacat gaagaatggt ttaatcacct cagcctataa   1260
cgtcatttct aaatcagctt tggtcggtat gggtgaaatt gtatctgaag atgcattagc   1320
ctggtacgaa tcacacccaa agcctttgca agcatctgaa ttgatcagta gattgcaaga   1380
tgacgttatg acttaccaat cgaaagagaa aagaggtcaa tctgctaccg gtgttgatgc   1440
atacatcaag acttacggtg tctcagaaaa gaaagcaatc gatgaattga agatcatgat   1500
cgaaaacgcc tggaaggaca ttaacgaagg ttgttttgaaa ccaagacaag tttctatgga   1560
tttgttagcc cctatattga atttggctag aatgatcgac gtcgtatata gatacgatga   1620
cggttttaca ttcccaggtt ccacattgaa agaatacata aacttgttgt tcgtagattc   1680
cttgccagtc tgaggcgcgc c                                             1701

SEQ ID NO: 4              moltype = DNA  length = 430
FEATURE                   Location/Qualifiers
misc_feature              1..430
                          note = TEF1
source                    1..430
                          mol_type = other DNA
                          organism = synthetic construct
SEQUENCE: 4
agtgatcccc cacacaccat agcttcaaaa tgtttctact cctttttac tcttccagat    60
tttctcggac tccgcgcatc gccgtaccac ttcaaaacac ccaagcacag catactaaat   120
ttcccctctt tcttcctcta gggtgtcgtt aattacccgt actaaaggtt tggaaaagaa   180
aaaagagacc gcctcgtttc ttttttcttcg tcgaaaaagg caataaaaat ttttatcacg   240
tttctttttc ttgaaaattt tttttttga tttttttcc tttcgatgac ctcccattga    300
tatttaagtt aataaacggt cttcaatttc tcaagtttca gtttcatttt tcttgttcta   360
ttacaacttt ttttacttct tgctcattag aaagaaagca tagcaatcta atctaagttt   420
taattacaaa                                                         430

SEQ ID NO: 5              moltype = DNA  length = 307
FEATURE                   Location/Qualifiers
misc_feature              1..307
                          note = CYC1t
source                    1..307
                          mol_type = other DNA
                          organism = synthetic construct
SEQUENCE: 5
ccgctgatcc tagagggccg catcatgtaa ttagttatgt cacgcttaca ttcacgccct    60
ccccccacat ccgctctaac cgaaaaggaa ggagttagac aacctgaagt ctaggtcccct  120
atttattttt ttatagttat gttagtatta agaacgttat ttatatttca aatttttctt   180
ttttttctgt acagacgcgt gtacgcatgt aacattatac tgaaaacctt gcttgagaag   240
gttttgggac gctcgaaggc tttaatttgc aagctgcggc cctgcattaa tgaatcggcc   300
aacgcgc                                                             307

SEQ ID NO: 6              moltype = DNA  length = 1047
FEATURE                   Location/Qualifiers
misc_feature              1..1047
                          note = ADH2
source                    1..1047
                          mol_type = other DNA
                          organism = synthetic construct
```

```
SEQUENCE: 6
atgtctattc cagaaactca aaaagccatt atcttctacg aatccaacgg caagttggag    60
cataaggata tcccagttcc aaagccaaag cccaacgaat tgttaatcaa cgtcaagtac   120
tctggtgtct gccacaccga tttgcacgct tggcatggtg actggccatt gccaactaag   180
ttaccattag ttggtggtca cgaaggtgcc ggtgtcgtta tcggcatggg tgaaaacgtt   240
aagggctgga gatcggtga ctacgccggt atcaaatggt tgaacggttc ttgtatggcc    300
tgtgaatact gtgaattggg taacgaatcc aactgtcctc acgctgactt gtctggttac   360
acccacgacg gttctttcca agaatacgct accgctgacg ctgttcaagc cgctcacatt   420
cctcaaggta ctgacttggc tgaagtcgcg ccaatcgttg tgctggtat caccgtatac    480
aaggctttga gtctgccaa cttgagagca ggccactggg cggccatttc tggtgctgct    540
ggtggtctag gttcttggc tgttcaatat gctaaggcga tgggttacag agtcttaggt    600
attgatggtg gtccaggaaa ggaagaattg tttacctcgc tcggtggtga agtattcatc   660
gacttcacca aagagaagga cattgttagc gcagtcgtta aggctaccaa cggcggtgcc   720
cacggtatca tcaatgtttc cgtttccgaa gccgctatcg aagcttctac cagatactgt   780
agggcgaacg gtactgttgt cttggttggt ttgccagccg tgcaaagtg ctcctctgat    840
gtcttcaacc acgttgtcaa gtctatctcc attgtcggct cttacgtggg gaacagagct   900
gataccagag aagccttaga tttctttgcc agaggtctag tcaagtctcc aataaaggta   960
gttggcttat ccagtttacc agaaatttac gaaaagatgg agaagggcca aattgctggt  1020
agatacgttg ttgacacttc taaataa                                      1047

SEQ ID NO: 7            moltype = DNA   length = 1503
FEATURE                 Location/Qualifiers
misc_feature            1..1503
                        note = ALD6
source                  1..1503
                        mol_type = other DNA
                        organism = synthetic construct
SEQUENCE: 7
atgactaagc tacactttga cactgctgaa ccagtcaaga tcacacttcc aaatggtttg    60
acatacgagc aaccaacgg tctattcatt aacaacaagt ttatgaaagc tcaagacggt   120
aagacctatc ccgtcgaaga tccttccact gaaaacaccg tttgtgaggt ctcttctgcc   180
accactgaag atgttgaata tgctatcgaa tgtgccgacc gtgctttcca cgacactgaa   240
tgggctaccc aagacccaag agaaagaggc cgtctactaa gtaagttggc tgacgaattg   300
gaaagccaaa ttgacttggt tcttccatt gaagctttgg acaatggtaa aactttggcc    360
ttagcccgtg gggatgttac cattgcaatc aactgctaa gagatgctgc tgcctatgcc    420
gacaaagtca acgtagaac aatcaacacc ggtgacggct acatgaactt caccacctta    480
gagccaatcg gtgtctgtgg tcaaattatt ccatggaact ttccaataat gatgttggct   540
tggaagatcg ccccagcatt ggccatgggt aacgtctgta tcttgaaacc cgctgctgtc   600
acacctttaa atgccctata ctttgcttct ttatgtaaga aggttggtat tccagctggt   660
gtcgtcaaca tcgttccagg tcctggtaga actgttggtg ctgctttgac caacgaccca   720
agaatcagaa agctggcttt taccggttct acagaagtcg gtaagagtgt tgctgtcgac   780
tcttctgaat ctaacttgaa gaaaatcact ttggaactag tggtaagtc cgcccatttg    840
gtctttgacg atgctaacat taagaagact ttaccaaatc tagtaaacgg tattttcaag   900
aacgctggtc aaatttgttc ctctggttct agaatttacg ttcaagaagg tatttacgac   960
gaactattgg ctgctttcaa ggcttacttg gaaaccgaaa tcaaagttgg taatccattt  1020
gacaaggcta acttccaagg tgctatcact aaccgtcaac aattcgacac aattatgaac  1080
tacatcgata tcggtaagaa agaaggcgcc aagatcttaa ctggtggcga aaagttggt   1140
gacaagggtt acttcatcag accaaccgtt ttctacgatg ttaatgaaga catgagaatt  1200
gttaaggaag aaattttttg gaccagttgtc actgtcgcaa agttcaagac tttagaagaa  1260
ggtgtcgaaa tggctaacag ctctgaattc ggtctaggtt ctggtatcga aacagaatct  1320
ttgagcacag gtttgaaggt ggccaagat ttgaaggccg taccgtctg gatcaacaca   1380
tacaacgatt ttgactccag agttccattc ggtggtgtta agcaatctgg ttacggtaga  1440
gaaatggggtg aagaagtcta ccatgcatac actgaagtaa agctgtcag aattaagttg  1500
taa                                                                 1503

SEQ ID NO: 8            moltype = DNA   length = 2142
FEATURE                 Location/Qualifiers
misc_feature            1..2142
                        note = ACS1
source                  1..2142
                        mol_type = other DNA
                        organism = synthetic construct
SEQUENCE: 8
atgtcgccct ctgccgtaca atcatcaaaa ctagaagaac agtcaagtga aattgacaag    60
ttgaaagcaa aaatgtccca gtctgccgcc actgcgcagc agaagaagga acatgagtat   120
gaacatttga cttcggtcaa gatcgtgcca caacggccca tctcagatag actgcagccc   180
gcaattgcta cccactattc tccacacttg acgggttgc aggactatca gcgcttgcac    240
aaggagtcta ttgaagaccc tgctaagttc ttcggttcta agctaccca atttttaaac   300
tggtctaagc cattcgataa ggtgttcatc ccagaccta aaacgggcag gccctccttc    360
cagaacaatg catggttcct caacggccaa ttaaacgcct gttacaactg tgttgacaga   420
catgccttga agactcctaa caagaaagcc attattttcg aaggtgacga gcctggccaa   480
ggctattcca ttacctacaa ggaactactt gaagaagttt gtcaagtggc acaagtgctg   540
acttactcta tgggcgttcg caagggcgat actgttgccg tgtacatgcc tatggttccca  600
gaagcaatca taacctgtt ggccatttcc cgtatcggtg ccattcactc cgtagtcttt   660
gccgggtttt cttccaactc cttgagagat cgtatcaacg atgggggactc taaagttgtc  720
atcactacag atgaatccaa cagagtggt aaagtcattg agactaaaag aattgttgat   780
gacgcgctaa gagagacccc aggcgtgaga cacgtcttgg tttatagaaa gaccaacaat   840
ccatctgttg cttttccatgc ccccagagat ttggattggg caacagaaaa agaaaaatac   900
aagacctact atcatgcac acccgttgat tctgaggatc cattattctt gttgtatacg   960
```

-continued

```
tctggttcta ctggtgcccc caagggtgtt caacattcta ccgcaggtta cttgctggga    1020
gctttgttga ccatgcgcta cacttttgac actcaccaag aagacgtttt cttcacagct    1080
ggagacattg gctggattac aggccacact tatgtggttt atggtccctt actatatggt    1140
tgtgccactt tggtctttga agggactcct gcgtacccaa attactcccg ttattgggat    1200
attattgatg aacacaaagt cacccaattt tatgttgcgc caactgcttt gcgtttgttg    1260
aaaagagctg gtgattccta catcgaaaat cattccttaa aatctttgcg ttgcttgggt    1320
tcggtcggtg agccaattgc tgctgaagtt tgggagtggt actctgaaaa aataggtaaa    1380
aatgaaatcc ccattgtaga cacctactgg caaacagaat ctggttcgca tctggtcacc    1440
ccgctggctg gtgtgttac accaatgaaa ccgggttctg cctcattccc cttcttcggt    1500
attgatgcag ttgttcttga ccctaacact ggtgaagaac ttaacaccag ccacgcagga    1560
ggtgtccttg ccgtcaaagc tgcatggcca tcatttgcaa gaactatttg gaaaaatcat    1620
gataggtatc tagacactta tttgaaccct taccctggct actatttcac tggtgatggt    1680
gctgcaaagg ataaggatgg ttatatctgg attttgggtc gtgtagacga tgtggtgaac    1740
gtctctgctg accgtctgtc taccgctgaa attgagctg ctattatcga agatccaatt    1800
gtggccgagt gtgctgttgt cggattcaac gatgacttga ctggtcaagc agttgctgca    1860
tttgtggtgt tgaaaaacaa atctagttgg tccaccgcaa cagatgatga attacaagat    1920
atcaagaagc atttggtctt tactgttaga aaagacatcg gccatttgc cgcaccaaaa    1980
ttgatcattt tagttggatga cttgcccaag acaagatccg gcaaaattat gagacgtatt    2040
ttaagaaaaa tcctagcagg agaaagtgac caactaggcg acgtttctac attgtcaaac    2100
cctggcattg ttagacatct aattgattcg gtcaagttgt aa                       2142

SEQ ID NO: 9             moltype = DNA   length = 1264
FEATURE                  Location/Qualifiers
misc_feature             1..1264
                         note = rDNA
source                   1..1264
                         mol_type = other DNA
                         organism = synthetic construct
SEQUENCE: 9
atgagagtag caaacgtaag tctaaaggtt gttttatagt agttaggatg tagaaaatgt      60
attccgatag gccattttac atttggaggg acgttgaaa gtggacagag aaaaggtgc     120
ggaaatggct gattttgatt gtttatgttt tgtgtgatga ttttacattt ttgcatagta    180
ttaggtagtc agatgaaaga tgaatagaca taggagtaag aaaacataga atagttaccg    240
ttattggtag gagtgtggtg gggtggtata gtccgcattg ggatgttact ttcctgttat    300
ggcatggatt tccctttagg gtctctgaag cgtatttccg tcaccgaaaa aggcagaaaa    360
agggaaactg aagggaggat agtagtaaag tttgaatggt ggtagtgtaa tgtatgatat    420
ccgttggttt tggtttcggt tgtgaaaagt tttttggtat gatattttgc aagtagcata    480
tatttcttgt gtgagaaagg tatatttgt atgttttgta tgtcccgcg cgtttccgta    540
ttttccgctt ccgcttccgc agtaaaaaat agtgaggaac tgggttaccc ggggcacctg    600
tcactttgga aaaaaaatat acgctaagat ttttggagaa tagcttaaat tgaagttttt    660
ctcggcgaga aatacgtagt taaggcagag cgacagagag ggcaaaagaa aataaaagta    720
agattttagt ttgtaatggg aggggggtt tagtcatgga gtacaagtgt gaggaaaagt    780
agttggaggg tacttcatgc gaaagcagtt gaagacaagt tcgaaaagag tttggaaacg    840
aattcgagta ggcttgtcgt tcgttatgtt tttgtaaatg gcctcgtcaa acggtggaga    900
gagtcgctag gtgatcgtca gatctgccta gtctctatac agcgtgttta attgacatgg    960
gttgatgcgt attgagagat acaatttggg aagaaattcc cagagtgtgt ttctttttgcg   1020
tttaacctga acagtctcat cgtgggcatc ttgcgattca attggtgagc agcgaaggat   1080
ttggtggatt actagctaat agcaatctat ttcaaagaat tcaaacttgg gggaatgcct   1140
tgttgaatag ccggtcgcaa gactgtgatt cttcaagtgt aacctcctct caaatcagcg   1200
atatcaaacg taccattccg tgaaacaccg gggtatctgt ttggtggaac ctgattagag   1260
gaaa                                                                 1264

SEQ ID NO: 10            moltype = DNA   length = 860
FEATURE                  Location/Qualifiers
misc_feature             1..860
                         note = TRP1
source                   1..860
                         mol_type = other DNA
                         organism = synthetic construct
SEQUENCE: 10
tacaatcttg atccggagct tttcttttt tgccgattaa gaattaattc ggtcgaaaaa      60
agaaaaggag agggccaaga gggagggcat tggtgactat tgagcacgtg agtatacgtg    120
attaagcaca caaaggcagc ttggagtatg tctgttatta atttcacagg tagttctggt    180
ccattggtga aagtttgcgg cttgcagagc acagaggccg cagaatgtgc tctagattcc    240
gatgctgact tgctgggtat tatatgtgtg cccaatagaa agagaacaat tgacccggtt    300
attcaaggaa aaatttcaag tcttgtaaaa gcatataaaa atagttcagg cactccgaaa    360
tacttggttg gcgtgtttcg taatcaacct aaggaggatg ttttggctct ggtcaatgat    420
tacggcattg atatcgtcca actgcatgga gatgagtcgt ggcaagaata ccaagagttc    480
ctcggtttgc cagttattaa aagactcgta tttccaaaag actgcaacat actactcagt    540
gcagcttcac agaaacctca ttcgtttatt cccttgtttg attcagaagc aggtgggaca    600
ggtgaacttt tggattggaa ctcgatttct gactgggttg gaaggcaaga gagccccgaa    660
agcttacatt tatgttagc tggtggactg acgccagaaa atgttggtga tgcgcttaga    720
ttaaatggcg ttattggtgt tgatgtaagc ggaggtgtgg agacaaatgg tgtaaaagac    780
tctaacaaaa tagcaaattt cgtcaaaaat gctaagaaat aggttattac tgagtagtat    840
ttatttaagt attgtttgtg                                                860

SEQ ID NO: 11            moltype = DNA   length = 1068
FEATURE                  Location/Qualifiers
misc_feature             1..1068
```

|  |  |  |
|---|---|---|
|  | note | = Polynucleotide |
| source | 1..1068 | |
|  | mol_type | = other DNA |
|  | organism | = synthetic construct |

SEQUENCE: 11

```
atggcttcag aaaaagaaat taggagagag agattcttga acgttttccc taaattagta    60
gaggaattga acgcatcgct tttggcttac ggtatgccta aggaagcatg tgactggtat   120
gcccactcat tgaactacaa cactccaggc ggtaagctaa atagaggttt gtccgttgtg   180
gacacgtatg ctattctctc caacaagacc gttgaacaat tggggcaaga agaatacgaa   240
aaggttgcca ttctaggttg gtgcattgag ttgttgcagg cttacttctt ggtcgccgat   300
gatatgatgg acaagtccat taccagaaga ggccaaccat gttggtacaa ggttcctgaa   360
gttggggaaa ttgccatcaa tgacgcattc atgttagagg ctgctatcta caagcttttg   420
aaatctcact tcagaaacga aaaatactac atagatatca ccgaattgtt ccatgaggtc   480
accttccaaa ccgaattggg ccaattgatg gacttaatca ctgcacctga agacaaagtc   540
gacttgagta agttctccct aaagaagcac tccttcatag ttactttcaa gactgcttac   600
tattctttct acttgcctgt cgcattggcc atgtacgttg ccggtatcac ggatgaaaag   660
gatttgaaac aagccagaga tgtcttgatt ccattgggtg aatacttcca aattcaagat   720
gactacttag actgcttcgg taccccagaa cagatcggta agcggtac agatatccaa   780
gataacaaat gttcttgggt aatcaacaag gcattggaac ttgcttccgc agaacaaaga   840
aagactttag acgaaaatta cggtaagaag gactcagtcg cagaagccaa atgcaaaaag   900
attttcaatg acttgaaaat tgaacagcta taccacgaat atgaagagtc tattgccaag   960
gatttgaagg ccaaaatttc tcaggtcgat gagtctcgtg gcttcaaagc tgatgtctta  1020
actgcgttct tgaacaaagt ttacaagaga agcaaaggtc gtgggttct  1068
```

| SEQ ID NO: 12 | moltype = DNA  length = 1686 |
|---|---|
| FEATURE | Location/Qualifiers |
| misc_feature | 1..1686 |
|  | note = Polynucleotide |
| source | 1..1686 |
|  | mol_type = other DNA |
|  | organism = synthetic construct |

SEQUENCE: 12

```
ggtggtggtt ctatggcagc agttgacact aatgccacca tccaagaaaa gaccaccgca    60
gagccggtgc gtcctttagc caacttccct cttcggtat ggggtgatcg cttcctatca   120
ttcactcttg acaattcgga actcgaagga tatgcaaaag ccatgaaagc cccaaaagaa   180
gaattgagaa gattgattgt agatcaaaca atggattcaa ataagaaact aagtttgatt   240
tattccgtcc accgtcttgg tttgacatat ctgttcttgc aagagattga agcccagcta   300
gacaaaattt tcaaagagtt caacttgcaa aattatgatg aagttgatct ttacacaact   360
tctatcaact ttcaagtttt ccgacacctt ggttataaac taccttgtga tgtgttaaac   420
aaattcaaag acaatacctc cggcgctttc aaggaagata tttctacgga tgtgaagggc   480
atgctaggct tatacgaatc ttcaacta agaacaagag gagaatcgat actagatgag   540
gcttcatcgt tcactgaaac taaactcaag agtgtagtaa acaatcttga aggaaatctt   600
gcacaacagg tgttacaatc attgaggaga ccatttcaa ggaggatgcc aatggtgaga   660
gcaaggctat atttctccaa ctatagtgaa gagtgtgcca cacatgagtg tttattaaag   720
cttgcaaagc tgcatttcag ctatttggag ctacagcaaa aggaagaact tcgcattgtc   780
tcaaagtggt ggaagatat gagattccag gaaactacac cttatataag ggatagagta   840
ccagagattt acttatggat tttgggattg tactttgagc ctcgttactc cttggcacga   900
atcatcgcca caaaaattac attgtttctt gtggtgctag atgatacata tgacgcttac   960
gctaccattg aagaaattcg acttttaact gatgccataa ataggtggga catgagtgct  1020
atggagcaaa ttccggaata cattagacca ttctacaaaa ttcctctaga tgagtatgct  1080
gagcttgaga acaactagc tatagaagga agagcaaaga gcgttattgc ttcaaagaa  1140
gcgttccaag acattgctag aggctacctt gaagaagccg agtggacaaa cagtgggtat  1200
gtggcatcat ttcctgagta catgaagaat gggttaatca cttcagccta caatgttatt  1260
tcgaaatctg ctttagtggg tatgggcgac atagttagtg aaaatgcatt ggcatggtac  1320
gaaagtcatc caaagactct acaagcttcc gagttaatct caagactcca agatgatgtc  1380
atgacttacc agtttgagcg tgaaagagga caatcagcca ctggagttga tgcgtatatc  1440
aagacatacg cgtgtcaga aaggaagct attgatgagc taaagataat gattgaaaat  1500
gcatggaaaa atataaacga gggatgtctc aagccaagag agtctcgat ggatttgctc  1560
gcgccaattc ttaaccttgc aagaatgata gatgttgtgt atcgatatga tgatgggttc  1620
accttcctg gaaaaccat gaaagagtat attactcttt tatttgttgg ttctgtatcc  1680
atgtaa                                                           1686
```

| SEQ ID NO: 13 | moltype = DNA  length = 1252 |
|---|---|
| FEATURE | Location/Qualifiers |
| misc_feature | 1..1252 |
|  | note = NDT80 |
| source | 1..1252 |
|  | mol_type = other DNA |
|  | organism = synthetic construct |

SEQUENCE: 13

```
gttcgaccat attgatgaag agtgggtagg ttataaaaga aattatttta ccttagtatc    60
aacgtttgaa acggcaaatt gtgatttgga tactttttta aagagcagtt ttgatcttct   120
cgttgaagac tcttcagtag aaagcagatt aagagtgcaa tatttcgcta tcaaaataaa   180
agctaagaat gacgacgacg acacggaaat caatctcgca cagcatacag cgaaacgcga   240
caaaggtcct caattttgtc cttcagtatg tccgttggtg ccttcccctt gccaaaaca   300
tcaaatcata agagaagctt caaatgttcg aaatatcact aaaatgaaaa aatacgattc   360
cacttttttat ttgcacagag accacgttaa ttatgaagaa tatggagtgg actctttatt   420
gttttcctat ccagaagatt ctattcagaa agttgcccgt tatgaaagag ttcaattgc   480
ttcatcaatt agcgtgaaga aaccatccca acaaaataaa cactttagct tgcatgtaat   540
```

```
tttaggtgca gtggtagatc cagataccct tcatggggag aatcccggaa ttccttatga    600
tgaactggct ttaaaaaatg gatcaaaagg gatgtttgtg tatttgcaag aaatgaaaac    660
gcctcctctt attattagag gaagatcacc ttctaactat gcgtcatctc agcgaataac    720
tgtgagaaca ccgtcgagtg tcaattcctc acaaaacagc acaaaagaa aaatgccatc     780
aattggcgag ccgttaaatg aaagttgctt aaatgcaaga ccttcgaaaa ggcgatccaa    840
agtggcgcta ggtgcaccga actctggggc ctccatctcg cctatcaaat ctcgtcaatc    900
cacaccaatg gaagcttcga aggaaaatga ggatccgttc ttcaggccaa ataaaagggt    960
ggagactctt gaacatatcc agaacaaact gggtgctttg aaaaatcaat gtccagattc   1020
ctctctgaaa tatccgagtt catcttcaag aggtatggaa gggtgtttag aaaaggagga   1080
tttagtttac tcaagtagtt tttctgttaa tatgaagcaa atcgaactga aaccggcacg   1140
ctcttttgaa catgagaata ttttcaaagt aggctcatta gcattcaaaa aaatcaatga   1200
attacctcat gaaaattatg atataacaat agagaagaaa tcaatggaac ag           1252
```

| SEQ ID NO: 14 | moltype = DNA  length = 1168 |
|---|---|
| FEATURE | Location/Qualifiers |
| misc_feature | 1..1168 |
| | note = HIS3 |
| source | 1..1168 |
| | mol_type = other DNA |
| | organism = synthetic construct |

SEQUENCE: 14
```
tcgcgcgttt cggtgatgac ggtgaaaacc tctgacacat gcagctcccg gagacggtca     60
cagcttgtct gtaagcggat gccgggagca gacaagcccg tcagggcgcg tcagcgggtg    120
ttggcgggtg tcgggctggc ttaactatgc ggcatcaga gcagattgta ctgagagtgc    180
accataattc cgttttaaga gcttggtgag cgctaggagt cactgccagg tatcgtttga    240
acacggcatt agtcagggaa gtcataacac agtcctttcc cgcaatttc ttttctattt    300
actcttggcc tcctctagta cactctatat ttttttatgc ctcggtaatg attttcattt    360
tttttttttcc acctagcgga tgactctttt ttttcttag cgattggcat tatcacataa     420
tgaattatac attatataaa gtaatgtgat ttcttcgaag aatatactaa aaaatgagca    480
ggcaagataa acgaaggcaa agatgacaga gcagaaagcc ctagtaaagc gtattacaaa    540
tgaaaccaag attcagattg cgatctcttt aaagggtggt cccctagcga tagagcactc    600
gatcttccca gaaaaagagg cagaagcagt agcagaacag gccacacaat cgcaagtgat    660
taacgtccac acaggtatag ggtttctgga ccatatgata catgctctgg ccaagcattc    720
cggctggtcg ctaatcgttg agtgcattgg tgacttacac atagacgacc atcacaccac    780
tgaagactgc gggattcagc tcgtcaagc ttttaaagag gccctactc gcgtggagt     840
aaaaaggttt ggatcaggat ttgcgccttt ggatgaggca cttttccagag cggtggtaga    900
tctttcgaac aggccgtacg cagttgtcga acttggtttg caagggaga aagtaggaga    960
tctctcttgc gagatgatcc cgcatttct tgaaagcttt gcagaggcta gcagaattac   1020
cctccacgtt gattgtctgc gaggcaagaa tgatcatcac cgtagtgaga gtgcgttcaa   1080
ggctccttgcg gttgccataa gagaagccac ctcgcccaat ggtaccaacg atgttccctc   1140
caccaaaggt gttcttatgt agtgacac                                      1168
```

| SEQ ID NO: 15 | moltype = AA  length = 4 |
|---|---|
| FEATURE | Location/Qualifiers |
| REGION | 1..4 |
| | note = Linker peptide |
| source | 1..4 |
| | mol_type = protein |
| | organism = synthetic construct |

SEQUENCE: 15
GGGS                                                                  4

| SEQ ID NO: 16 | moltype = AA  length = 4 |
|---|---|
| FEATURE | Location/Qualifiers |
| REGION | 1..4 |
| | note = Linker peptide 4A001 |
| source | 1..4 |
| | mol_type = protein |
| | organism = synthetic construct |

SEQUENCE: 16
PGGH                                                                  4

| SEQ ID NO: 17 | moltype = AA  length = 5 |
|---|---|
| FEATURE | Location/Qualifiers |
| REGION | 1..5 |
| | note = Linker peptide 5A002 |
| source | 1..5 |
| | mol_type = protein |
| | organism = synthetic construct |

SEQUENCE: 17
YRSQI                                                                 5

| SEQ ID NO: 18 | moltype = AA  length = 6 |
|---|---|
| FEATURE | Location/Qualifiers |
| REGION | 1..6 |
| | note = Linker peptide 6A005 |
| source | 1..6 |
| | mol_type = protein |
| | organism = synthetic construct |

-continued

```
SEQUENCE: 18
VIPFIS                                                                         6

SEQ ID NO: 19           moltype = AA   length = 6
FEATURE                 Location/Qualifiers
REGION                  1..6
                        note = Linker peptide 6B004
source                  1..6
                        mol_type = protein
                        organism = synthetic construct
SEQUENCE: 19
FLYLKF                                                                         6

SEQ ID NO: 20           moltype = AA   length = 8
FEATURE                 Location/Qualifiers
REGION                  1..8
                        note = Linker peptide 8A005
source                  1..8
                        mol_type = protein
                        organism = synthetic construct
SEQUENCE: 20
WRFSPKLQ                                                                       8

SEQ ID NO: 21           moltype = AA   length = 12
FEATURE                 Location/Qualifiers
REGION                  1..12
                        note = Linker peptide 12A003
source                  1..12
                        mol_type = protein
                        organism = synthetic construct
SEQUENCE: 21
HHVQESQCIS TV                                                                 12

SEQ ID NO: 22           moltype = DNA   length = 36
FEATURE                 Location/Qualifiers
misc_feature            1..36
                        note = Primer SexA1-ADH2
source                  1..36
                        mol_type = other DNA
                        organism = synthetic construct
SEQUENCE: 22
gcgaccwggt atgtctattc cagaaactca aaaagc                                       36

SEQ ID NO: 23           moltype = DNA   length = 36
FEATURE                 Location/Qualifiers
misc_feature            1..36
                        note = Primer ADH2-Asc1
source                  1..36
                        mol_type = other DNA
                        organism = synthetic construct
SEQUENCE: 23
gcggcgcgcc ttatttagaa gtgtcaacaa cgtatc                                       36

SEQ ID NO: 24           moltype = DNA   length = 39
FEATURE                 Location/Qualifiers
misc_feature            1..39
                        note = Primer SexA1-ALD6
source                  1..39
                        mol_type = other DNA
                        organism = synthetic construct
SEQUENCE: 24
tcgcgaccwg gtaaaacaat gactaagcta cactttgac                                    39

SEQ ID NO: 25           moltype = DNA   length = 34
FEATURE                 Location/Qualifiers
misc_feature            1..34
                        note = Primer ALD6-Asc1
source                  1..34
                        mol_type = other DNA
                        organism = synthetic construct
SEQUENCE: 25
tcgcggcgcg ccttacaact taattctgac agct                                         34

SEQ ID NO: 26           moltype = DNA   length = 41
FEATURE                 Location/Qualifiers
misc_feature            1..41
                        note = Primer SexA1-ACS1
source                  1..41
                        mol_type = other DNA
```

```
                        organism = synthetic construct
SEQUENCE: 26
tcgcgaccwg gtaaaacaat gtcgccctct gccgtacaat c                    41

SEQ ID NO: 27           moltype = DNA  length = 36
FEATURE                 Location/Qualifiers
misc_feature            1..36
                        note = Primer ACS1-Asc1
source                  1..36
                        mol_type = other DNA
                        organism = synthetic construct
SEQUENCE: 27
tcgcggcgcg ccttacaact tgaccgaatc aattag                          36

SEQ ID NO: 28           moltype = DNA  length = 34
FEATURE                 Location/Qualifiers
misc_feature            1..34
                        note = Primer Sac11-TEF1
source                  1..34
                        mol_type = other DNA
                        organism = synthetic construct
SEQUENCE: 28
gcgccgcgga gtgatccccc acacaccata gctt                            34

SEQ ID NO: 29           moltype = DNA  length = 36
FEATURE                 Location/Qualifiers
misc_feature            1..36
                        note = Primer TEF1-SexA1
source                  1..36
                        mol_type = other DNA
                        organism = synthetic construct
SEQUENCE: 29
tggcgaccwg gttttgtaat taaaacttag attaga                          36

SEQ ID NO: 30           moltype = DNA  length = 34
FEATURE                 Location/Qualifiers
misc_feature            1..34
                        note = Primer BamH1-pMF1
source                  1..34
                        mol_type = other DNA
                        organism = synthetic construct
SEQUENCE: 30
gcgggatccg ggaagacatg cttaacaaga agat                            34

SEQ ID NO: 31           moltype = DNA  length = 35
FEATURE                 Location/Qualifiers
misc_feature            1..35
                        note = Primer pMF1-SexA1
source                  1..35
                        mol_type = other DNA
                        organism = synthetic construct
SEQUENCE: 31
gcgacctggt tcttttaatc gtttatattg tgtat                           35

SEQ ID NO: 32           moltype = DNA  length = 35
FEATURE                 Location/Qualifiers
misc_feature            1..35
                        note = Primer Asc1-CYC1
source                  1..35
                        mol_type = other DNA
                        organism = synthetic construct
SEQUENCE: 32
gcggcgcgcc ccgctgatcc tagagggccg catca                           35

SEQ ID NO: 33           moltype = DNA  length = 34
FEATURE                 Location/Qualifiers
misc_feature            1..34
                        note = Primer CYC1-Sac11
source                  1..34
                        mol_type = other DNA
                        organism = synthetic construct
SEQUENCE: 33
gcgccgcggg cgcgttggcc gattcattaa tgca                            34

SEQ ID NO: 34           moltype = DNA  length = 42
FEATURE                 Location/Qualifiers
misc_feature            1..42
                        note = Primer SEXA1-ERG20
source                  1..42
```

```
                              -continued
                        mol_type = other DNA
                        organism = synthetic construct
SEQUENCE: 34
gcgaccwggt aaacaatgg cttcagaaaa agaaattagg ag                         42

SEQ ID NO: 35           moltype = DNA   length = 46
FEATURE                 Location/Qualifiers
misc_feature            1..46
                        note = Primer ERG20-GGGS
source                  1..46
                        mol_type = other DNA
                        organism = synthetic construct
SEQUENCE: 35
cttttcccata gaaccaccac cctatttgct tctcttgtaa actttg                   46

SEQ ID NO: 36           moltype = DNA   length = 32
FEATURE                 Location/Qualifiers
misc_feature            1..32
                        note = Primer GGGS-LSLTC2
source                  1..32
                        mol_type = other DNA
                        organism = synthetic construct
SEQUENCE: 36
ggtggtggtt ctatggcagc agttgacact aa                                   32

SEQ ID NO: 37           moltype = DNA   length = 36
FEATURE                 Location/Qualifiers
misc_feature            1..36
                        note = Primer LSLTC2-ASC1
source                  1..36
                        mol_type = other DNA
                        organism = synthetic construct
SEQUENCE: 37
gcgggcgcgc cttacatgga tacagaacca acaaat                               36

SEQ ID NO: 38           moltype = DNA   length = 21
FEATURE                 Location/Qualifiers
misc_feature            1..21
                        note = Primer V313-to-R
source                  1..21
                        mol_type = other DNA
                        organism = synthetic construct
SEQUENCE: 38
ctttgccttc gtttatcttg c                                               21

SEQ ID NO: 39           moltype = DNA   length = 24
FEATURE                 Location/Qualifiers
misc_feature            1..24
                        note = Primer V313-to-F
source                  1..24
                        mol_type = other DNA
                        organism = synthetic construct
SEQUENCE: 39
tatatgtata cctatgaatg tcag                                            24

SEQ ID NO: 40           moltype = DNA   length = 38
FEATURE                 Location/Qualifiers
misc_feature            1..38
                        note = Primer Bsp-Leu-F
source                  1..38
                        mol_type = other DNA
                        organism = synthetic construct
SEQUENCE: 40
tggcgtccgg attaagcaag gattttctta acttcttc                             38

SEQ ID NO: 41           moltype = DNA   length = 35
FEATURE                 Location/Qualifiers
misc_feature            1..35
                        note = Primer Bsp-Leu-R
source                  1..35
                        mol_type = other DNA
                        organism = synthetic construct
SEQUENCE: 41
tggcgtccgg agatgcggta ttttctcctt acgca                                35

SEQ ID NO: 42           moltype = DNA   length = 36
FEATURE                 Location/Qualifiers
misc_feature            1..36
                        note = Primer SexA1-SynSmFPS
```

```
source                      1..36
                            mol_type = other DNA
                            organism = synthetic construct
SEQUENCE: 42
acctggtaaa acaatggcta atttgaatgg tgaatc                              36

SEQ ID NO: 43               moltype = DNA  length = 45
FEATURE                     Location/Qualifiers
misc_feature                1..45
                            note = Primer SynSmFPS-GGGS
source                      1..45
                            mol_type = other DNA
                            organism = synthetic construct
SEQUENCE: 43
tgctgccata gaaccaccac cttttttgtct tttatagatt ttacc                   45

SEQ ID NO: 44               moltype = DNA  length = 35
FEATURE                     Location/Qualifiers
misc_feature                1..35
                            note = Primer GGGS-STpGMAS
source                      1..35
                            mol_type = other DNA
                            organism = synthetic construct
SEQUENCE: 44
ggtggtggtt ctatggcagc agtacaagca accac                               35

SEQ ID NO: 45               moltype = DNA  length = 28
FEATURE                     Location/Qualifiers
misc_feature                1..28
                            note = Primer STpGMAS-Asc1
source                      1..28
                            mol_type = other DNA
                            organism = synthetic construct
SEQUENCE: 45
ggcgcgcctc agactggcaa ggaatcta                                       28

SEQ ID NO: 46               moltype = DNA  length = 41
FEATURE                     Location/Qualifiers
misc_feature                1..41
                            note = Primer NDT80-up-PmeI
source                      1..41
                            mol_type = other DNA
                            organism = synthetic construct
SEQUENCE: 46
gcggtttaaa cgttcgacca tattgatgaa gagtgggtag g                        41

SEQ ID NO: 47               moltype = DNA  length = 33
FEATURE                     Location/Qualifiers
misc_feature                1..33
                            note = Primer NDT80-down
source                      1..33
                            mol_type = other DNA
                            organism = synthetic construct
SEQUENCE: 47
ctgttccatt gatttcttct ctattgttat atc                                 33

SEQ ID NO: 48               moltype = DNA  length = 33
FEATURE                     Location/Qualifiers
misc_feature                1..33
                            note = Primer Bsp-HIS-F
source                      1..33
                            mol_type = other DNA
                            organism = synthetic construct
SEQUENCE: 48
tggcgtccgg atcgcgcgtt tcggtgatga cgg                                 33

SEQ ID NO: 49               moltype = DNA  length = 33
FEATURE                     Location/Qualifiers
misc_feature                1..33
                            note = Primer Pme1-HIS-R
source                      1..33
                            mol_type = other DNA
                            organism = synthetic construct
SEQUENCE: 49
gcggtttaaa cgtgtcacta cataagaaca cct                                 33

SEQ ID NO: 50               moltype = DNA  length = 23
FEATURE                     Location/Qualifiers
misc_feature                1..23
```

```
                           note = Primer rDNA-up-F
source                     1..23
                           mol_type = other DNA
                           organism = synthetic construct
SEQUENCE: 50
atgagagtag caaacgtaag tct                                                 23

SEQ ID NO: 51              moltype = DNA  length = 34
FEATURE                    Location/Qualifiers
misc_feature               1..34
                           note = Primer rDNA-R-PmeI
source                     1..34
                           mol_type = other DNA
                           organism = synthetic construct
SEQUENCE: 51
gcggtttaaa ctttcctcta atcaggttcc acca                                     34

SEQ ID NO: 52              moltype = DNA  length = 31
FEATURE                    Location/Qualifiers
misc_feature               1..31
                           note = Primer BSP-TRP1-F
source                     1..31
                           mol_type = other DNA
                           organism = synthetic construct
SEQUENCE: 52
tggcgtccgg atacaatctt gatccggagc t                                        31

SEQ ID NO: 53              moltype = DNA  length = 35
FEATURE                    Location/Qualifiers
misc_feature               1..35
                           note = Primer BSP-TRP1-R
source                     1..35
                           mol_type = other DNA
                           organism = synthetic construct
SEQUENCE: 53
tggcgtccgg acacaaacaa tacttaaata aatac                                    35

SEQ ID NO: 54              moltype = DNA  length = 74
FEATURE                    Location/Qualifiers
misc_feature               1..74
                           note = Primer X1-M-pEASY-r-t-F
source                     1..74
                           mol_type = other DNA
                           organism = synthetic construct
SEQUENCE: 54
cttgcaaatg cctattgtgc agatgttata atatctgtgc gtttaattaa ggctcgtatg         60
ttgtgtggaa ttgt                                                           74

SEQ ID NO: 55              moltype = DNA  length = 30
FEATURE                    Location/Qualifiers
misc_feature               1..30
                           note = Primer NDT80-interg-2
source                     1..30
                           mol_type = other DNA
                           organism = synthetic construct
SEQUENCE: 55
ctggctttaa aaaatggata aaaagggatg                                          30

SEQ ID NO: 56              moltype = DNA  length = 80
FEATURE                    Location/Qualifiers
misc_feature               1..80
                           note = Primer 1-M-pEASY-PGK1-F
source                     1..80
                           mol_type = other DNA
                           organism = synthetic construct
SEQUENCE: 56
ctgtttcctg tgtgaaattg ttatccgctc acaattccac acaacatacg agccttaatt         60
aaacgcacag atattataac                                                     80

SEQ ID NO: 57              moltype = DNA  length = 75
FEATURE                    Location/Qualifiers
misc_feature               1..75
                           note = Primer 3G-1-M-ADHt-TDH3-R
source                     1..75
                           mol_type = other DNA
                           organism = synthetic construct
SEQUENCE: 57
cctccgcgtc attaaacttc ttgttgttga cgctaacatt caacgctagt attcggcatg         60
ccggtagagg tgtgg                                                          75
```

```
SEQ ID NO: 58         moltype = DNA  length = 76
FEATURE               Location/Qualifiers
misc_feature          1..76
                      note = Primer 3G-3-M-ADHt-TDH3-F
source                1..76
                      mol_type = other DNA
                      organism = synthetic construct
SEQUENCE: 58
caggtatagc atgaggtcgc tcttattgac cacacctcta ccggcatgcc gaatactagc    60
gttgaatgtt agcgtc                                                   76

SEQ ID NO: 59         moltype = DNA  length = 75
FEATURE               Location/Qualifiers
misc_feature          1..75
                      note = Primer 3G-3-M-TPI1t-TEF1-R
source                1..75
                      mol_type = other DNA
                      organism = synthetic construct
SEQUENCE: 59
aggagtagaa acattttgaa gctatggtgt gtgggggatc actttaatta atctatataa    60
cagttgaaat ttgga                                                    75

SEQ ID NO: 60         moltype = DNA  length = 76
FEATURE               Location/Qualifiers
misc_feature          1..76
                      note = Primer 3G-2-M-TPI1t-TEF1-F
source                1..76
                      mol_type = other DNA
                      organism = synthetic construct
SEQUENCE: 60
gtcattttcg cgttgagaag atgttcttat ccaaatttca actgttatat agattaatta    60
aagtgatccc ccacac                                                   76

SEQ ID NO: 61         moltype = DNA  length = 78
FEATURE               Location/Qualifiers
misc_feature          1..78
                      note = Primer M-CYC1-pEASY-R
source                1..78
                      mol_type = other DNA
                      organism = synthetic construct
SEQUENCE: 61
cgtattacaa ttcactggcc gtcgttttac aacgtcgtga ctgggaaaac cctggcgcgt    60
tggccgattc attaatgc                                                 78

SEQ ID NO: 62         moltype = DNA  length = 30
FEATURE               Location/Qualifiers
misc_feature          1..30
                      note = Primer NDT80-interg-1
source                1..30
                      mol_type = other DNA
                      organism = synthetic construct
SEQUENCE: 62
catcataagg aattccggga ttctccccat                                    30

SEQ ID NO: 63         moltype = DNA  length = 79
FEATURE               Location/Qualifiers
misc_feature          1..79
                      note = Primer X2-M-pEASY-r-t-R
source                1..79
                      mol_type = other DNA
                      organism = synthetic construct
SEQUENCE: 63
cgaaggcttt aatttgcaag ctgcggccct gcattaatga atcggccaac gcgccagggt    60
tttcccagtc acgacgttg                                                79

SEQ ID NO: 64         moltype = DNA  length = 12
FEATURE               Location/Qualifiers
misc_feature          1..12
                      note = Nucleotide sequence for linker peptide 4A001
source                1..12
                      mol_type = other DNA
                      organism = synthetic construct
SEQUENCE: 64
ccgggggggac ac                                                      12

SEQ ID NO: 65         moltype = DNA  length = 15
FEATURE               Location/Qualifiers
misc_feature          1..15
```

```
                    note = Nucleotide sequence for linker peptide 5A002
source              1..15
                    mol_type = other DNA
                    organism = synthetic construct
SEQUENCE: 65
tatagaagtc aaatc                                                         15

SEQ ID NO: 66       moltype = DNA   length = 18
FEATURE             Location/Qualifiers
misc_feature        1..18
                    note = Nucleotide sequence for linker peptide 6A005
source              1..18
                    mol_type = other DNA
                    organism = synthetic construct
SEQUENCE: 66
gtgataccttt ttatttca                                                     18

SEQ ID NO: 67       moltype = DNA   length = 18
FEATURE             Location/Qualifiers
misc_feature        1..18
                    note = Nucleotide sequence for linker peptide 6B004
source              1..18
                    mol_type = other DNA
                    organism = synthetic construct
SEQUENCE: 67
tttttgtatc ttaagttt                                                      18

SEQ ID NO: 68       moltype = DNA   length = 24
FEATURE             Location/Qualifiers
misc_feature        1..24
                    note = Nucleotide sequence for linker peptide 8A005
source              1..24
                    mol_type = other DNA
                    organism = synthetic construct
SEQUENCE: 68
tggcggttct cgccgaagct tcag                                               24

SEQ ID NO: 69       moltype = DNA   length = 36
FEATURE             Location/Qualifiers
misc_feature        1..36
                    note = Nucleotide sequence for linker peptide 12A003
source              1..36
                    mol_type = other DNA
                    organism = synthetic construct
SEQUENCE: 69
caccacgtgc aggagtcaca atgtatttcc acagtg                                  36

SEQ ID NO: 70       moltype = DNA   length = 80
FEATURE             Location/Qualifiers
misc_feature        1..80
                    note = Primer 50bp-3A001-STpGmA
source              1..80
                    mol_type = other DNA
                    organism = synthetic construct
SEQUENCE: 70
caagcagttt tgaaatcatt tttgggtaaa atctataaaa gacaaaaata cggtcagatg        60
gcagcagtac aagcaaccac                                                    80

SEQ ID NO: 71       moltype = DNA   length = 24
FEATURE             Location/Qualifiers
misc_feature        1..24
                    note = Primer SynSmFPS-Linker-R
source              1..24
                    mol_type = other DNA
                    organism = synthetic construct
SEQUENCE: 71
tttttgtctt ttatagattt tacc                                               24

SEQ ID NO: 72       moltype = DNA   length = 83
FEATURE             Location/Qualifiers
misc_feature        1..83
                    note = Primer 50bp-4A001-STpGmA
source              1..83
                    mol_type = other DNA
                    organism = synthetic construct
SEQUENCE: 72
caagcagttt tgaaatcatt tttgggtaaa atctataaaa gacaaaaacc gggggggacac       60
atggcagcag tacaagcaac cac                                                83
```

```
SEQ ID NO: 73            moltype = DNA  length = 86
FEATURE                  Location/Qualifiers
misc_feature             1..86
                         note = Primer 50bp-5A002-STpGmA
source                   1..86
                         mol_type = other DNA
                         organism = synthetic construct
SEQUENCE: 73
caagcagttt tgaaatcatt tttgggtaaa atctataaaa gacaaaaata tagaagtcaa   60
atcatggcag cagtacaagc aaccac                                       86

SEQ ID NO: 74            moltype = DNA  length = 89
FEATURE                  Location/Qualifiers
misc_feature             1..89
                         note = Primer 50bp-6A005-STpGmA
source                   1..89
                         mol_type = other DNA
                         organism = synthetic construct
SEQUENCE: 74
caagcagttt tgaaatcatt tttgggtaaa atctataaaa gacaaaaagt gataccttt   60
atttcaatgg cagcagtaca agcaaccac                                    89

SEQ ID NO: 75            moltype = DNA  length = 89
FEATURE                  Location/Qualifiers
misc_feature             1..89
                         note = Primer 50bp-6B004-STpGmA
source                   1..89
                         mol_type = other DNA
                         organism = synthetic construct
SEQUENCE: 75
caagcagttt tgaaatcatt tttgggtaaa atctataaaa gacaaaaatt tttgtatctt   60
aagtttatgg cagcagtaca agcaaccac                                    89

SEQ ID NO: 76            moltype = DNA  length = 95
FEATURE                  Location/Qualifiers
misc_feature             1..95
                         note = Primer 50bp-8A005-STpGmA
source                   1..95
                         mol_type = other DNA
                         organism = synthetic construct
SEQUENCE: 76
caagcagttt tgaaatcatt tttgggtaaa atctataaaa gacaaaaatg gcggttctcg   60
ccgaagcttc agatggcagc agtacaagca accac                             95

SEQ ID NO: 77            moltype = DNA  length = 107
FEATURE                  Location/Qualifiers
misc_feature             1..107
                         note = Primer 50bp-12A003-STpGmA
source                   1..107
                         mol_type = other DNA
                         organism = synthetic construct
SEQUENCE: 77
caagcagttt tgaaatcatt tttgggtaaa atctataaaa gacaaaaaca ccacgtgcag   60
gagtcacaat gtatttccac agtgatggca gcagtacaag caaccac                107

SEQ ID NO: 78            moltype = DNA  length = 26
FEATURE                  Location/Qualifiers
misc_feature             1..26
                         note = Primer X1-r-t-R-rDNA
source                   1..26
                         mol_type = other DNA
                         organism = synthetic construct
SEQUENCE: 78
ctcactattt tttactgcgg aagcgg                                       26

SEQ ID NO: 79            moltype = DNA  length = 70
FEATURE                  Location/Qualifiers
misc_feature             1..70
                         note = Primer 1-M-ADHt-TEF1-R
source                   1..70
                         mol_type = other DNA
                         organism = synthetic construct
SEQUENCE: 79
ggagtagaaa cattttgaag ctatggtgtg tgggggatca ctttaattaa tcggcatgcc   60
ggtagaggtg                                                         70

SEQ ID NO: 80            moltype = DNA  length = 70
FEATURE                  Location/Qualifiers
misc_feature             1..70
```

|  | note = Primer 2-M-ADHt-TEF1-F |
|---|---|
| source | 1..70 |
|  | mol_type = other DNA |
|  | organism = synthetic construct |

SEQUENCE: 80
ggtatagcat gaggtcgctc ttattgacca cacctctacc ggcatgccga ttaattaaag 60
tgatccccca 70

| SEQ ID NO: 81 | moltype = DNA   length = 26 |
|---|---|
| FEATURE | Location/Qualifiers |
| misc_feature | 1..26 |
|  | note = Primer X2-r-t-F-rDNA |
| source | 1..26 |
|  | mol_type = other DNA |
|  | organism = synthetic construct |

SEQUENCE: 81
gaactgggtt acccggggca cctgtc 26